United States Patent
Gorbunov et al.

(10) Patent No.: US 10,792,694 B2
(45) Date of Patent: *Oct. 6, 2020

(54) CONDENSATION APPARATUS

(71) Applicant: PARTICLE MEASURING SYSTEMS INC., Boulder, CO (US)

(72) Inventors: Boris Zachar Gorbunov, Canterbury (GB); Harald Wilhelm Julius Gnewuch, Canterbury (GB)

(73) Assignee: PARTICLE MEASURING SYSTEMS, INC., Boulder, CO (US)

(*) Notice: Subject to any disclaimer, the term of this patent is extended or adjusted under 35 U.S.C. 154(b) by 91 days.

This patent is subject to a terminal disclaimer.

(21) Appl. No.: 15/867,672

(22) Filed: Jan. 10, 2018

(65) Prior Publication Data

US 2018/0133744 A1 May 17, 2018

Related U.S. Application Data

(63) Continuation of application No. 14/485,221, filed on Sep. 12, 2014, now abandoned, which is a
(Continued)

(30) Foreign Application Priority Data

May 8, 2008 (GB) .................................. 0808385.9

(51) Int. Cl.
*B05C 3/00* (2006.01)
*G01N 15/02* (2006.01)
(Continued)

(52) U.S. Cl.
CPC ............ *B05C 3/005* (2013.01); *B01D 5/0027* (2013.01); *B05C 3/02* (2013.01); *G01N 15/02* (2013.01);
(Continued)

(58) Field of Classification Search
CPC .. G01N 15/065; G01N 15/02; G01N 33/0011; G01N 2015/0046; B05C 3/005;
(Continued)

(56) References Cited

U.S. PATENT DOCUMENTS 4,790,650 A 12/1988 Keady
4,948,511 A 8/1990 Swanson et al.
(Continued)

FOREIGN PATENT DOCUMENTS

CN 102089640 A 6/2011
CN 105311848 A 2/2016
(Continued)

OTHER PUBLICATIONS

U.S. Appl. No. 12/991,535, filed Nov. 8, 2010.
(Continued)

*Primary Examiner* — Yuechuan Yu
(74) *Attorney, Agent, or Firm* — Leydig, Voit & Mayer, Ltd.

(57) ABSTRACT

Apparatuses for increasing the effective size of gas-entrained particles in a particle detector are disclosed. In one embodiment, an apparatus comprises an evaporation chamber, a condenser in fluid communication with the evaporation chamber, and an inlet in fluid communication with the condenser for receiving a stream of sample gas containing gas-entrained particles. The evaporation chamber includes a heating element and a porous support surrounding the heating element. The porous support carries thereon a working fluid, and the heating element vaporizes the working fluid to form vapor within the evaporation chamber. The porous support may include a portion which extends into a working fluid reservoir.

21 Claims, 19 Drawing Sheets

Related U.S. Application Data continuation of application No. 12/991,535, filed as application No. PCT/GB2009/001147 on May 8, 2009, now Pat. No. 8,869,593.

(51) Int. Cl.

| | | |
|---|---|---|
| *B01D 5/00* | (2006.01) | |
| *G01N 15/06* | (2006.01) | |
| *B05C 3/02* | (2006.01) | |
| *G01N 33/00* | (2006.01) | |
| *G01N 15/00* | (2006.01) | |

(52) U.S. Cl.
CPC ....... *G01N 15/065* (2013.01); *G01N 33/0011* (2013.01); *G01N 2015/0046* (2013.01); *Y10T 137/6416* (2015.04); *Y10T 137/8593* (2015.04)

(58) Field of Classification Search
CPC ... B05C 3/02; B01D 5/0027; Y10T 137/6416; Y10T 137/8593
See application file for complete search history.

(56) References Cited

U.S. PATENT DOCUMENTS

| | | | |
|---|---|---|---|
| 5,239,356 | A | 8/1993 | Hollander et al. |
| 5,247,158 | A * | 9/1993 | Steinhauser ............. H05B 3/46 219/534 |
| 5,632,329 | A * | 5/1997 | Fay ........................... F28B 1/06 165/113 |
| 5,675,405 | A | 10/1997 | Schildmeyer et al. |
| 6,498,641 | B1 | 12/2002 | Schildmeyer |
| 6,506,345 | B1 | 1/2003 | Lee et al. |
| 6,567,157 | B1 | 5/2003 | Flagan et al. |
| 7,850,908 | B1 | 12/2010 | Wick |
| 8,869,593 | B2 | 10/2014 | Gorbunov et al. |
| 2001/0050055 | A1 * | 12/2001 | Horiuchi ................. B01J 2/006 118/716 |
| 2003/0202169 | A1 | 10/2003 | Liu |
| 2007/0232706 | A1 | 10/2007 | Shah et al. |
| 2008/0173585 | A1 | 7/2008 | White et al. |
| 2009/0031786 | A1 | 2/2009 | Takeuchi et al. |
| 2009/0031828 | A1 | 2/2009 | Ulevicius et al. |
| 2009/0183554 | A1 | 7/2009 | Grant et al. |
| 2015/0000595 | A1 | 1/2015 | Gorbunov et al. |

FOREIGN PATENT DOCUMENTS

| | | | | |
|---|---|---|---|---|
| DE | 102005044660 | A1 * | 3/2007 | ............ B01B 1/005 |
| EP | 1757921 | A2 | 2/2007 | |
| EP | 1879016 | A2 | 1/2008 | |
| EP | 2279402 | A1 | 2/2011 | |
| EP | 2629080 | B1 | 4/2016 | |
| EP | 2623954 | B1 | 8/2016 | |
| JP | 5677287 | B2 | 2/2015 | |
| JP | 5955939 | B2 | 7/2016 | |
| JP | 6258393 | B2 | 1/2018 | |
| WO | WO 2002/029382 | A1 | 4/2002 | |
| WO | WO 03/078971 | A1 | 9/2003 | |
| WO | WO 2004/089499 | A2 | 10/2004 | |
| WO | WO 2005/066610 | A1 | 7/2005 | |
| WO | WO 2006/037320 | A1 | 4/2006 | |
| WO | WO 2007/010698 | A1 | 1/2007 | |
| WO | WO 2009/136166 | A1 | 11/2009 | |
| WO | WO 2010/014520 | A1 | 2/2010 | |

OTHER PUBLICATIONS

U.S. Appl. No. 14/485,221, filed Sep. 12, 2014.
Chinese First Office Action, English translation, dated Aug. 22, 2012, in Chinese Patent Application No. 2009/80126900.8, 5 pp.
Chinese Second Office Action, English translation, dated Apr. 16, 2013, in Chinese Patent Application No. 2009/80126900.8, 5 pp.
Chinese Third Office Action, English translation, dated Dec. 31, 2013, in Chinese Patent Application No. 2009/80126900.8, 4 pp.
Chinese Fourth Office Action, English translation, dated Aug. 26, 2014, in Chinese Patent Application No. 2009/80126900.8, 4 pp.
Chinese First Office Action, English translation, dated Dec. 26, 2016, in Chinese Patent Application No. 201510176741.X, 9 pp.
EP Office Action, dated Aug. 2, 2011, in European Patent Application No. 09 742 362.8, 6 pp.
EP Office Action, dated Aug. 16, 2012, in European Patent Application No. 09 742 362.8, 5 pp.
EP Office Action, dated Jul. 3, 2015, in European Patent Application No. 13 166 062.3, 4 pp.
EP Office Action, dated Jul. 3, 2015, in European Patent Application No. 13 168 356.7, 4 pp.
European Search Report, dated Oct. 14, 2013, corresponding to European Application No. 13 166 062.3, 11 pp.
European Search Report, dated Nov. 21, 2013, corresponding to European Application No. 13 168 356.7, 13 pp.
Gallar et al. (2006) "A Variable Supersaturation Condensation Particle Sizer," Aerosol Science and Technology 40: 431-436.
Hering et al. (2005) "A Laminar-Flow, Water-Based Condensation Particle Counter (WCPC)," Aerosol Science and Technology 39: 659-672.
International Search Report for PCT/GB2009/001147, dated Oct. 15, 2009.
International Search Report for PCT/US2009/051792, dated Nov. 12, 2009.
Partial European Search Report, dated Jun. 26, 2013, corresponding to European Application No. 13 168 356.7, 7 pp.
Partial European Search Report, dated Jul. 2, 2013, corresponding to European Application No. 13 166 062.3, 6 pp.

* cited by examiner

- - PRIOR ART - -

CONDENSATION APPARATUS

CROSS REFERENCE TO RELATED APPLICATIONS

This application is a continuation of U.S. patent application Ser. No. 14/485,221, filed on Sep. 12, 2014, which is a continuation of U.S. patent application Ser. No. 12/991,535, filed Nov. 8, 2010, now U.S. Pat. No. 8,869,593 which issued on Oct. 28, 2014, which is a 35 U.S.C. § 371 filing of International Application No. PCT/GB2009/001147, filed May 8, 2009, which claims the benefit of and priority to United Kingdom Patent Application No. 0808385.9, filed May 8, 2008, each of which is hereby incorporated by reference in its entirety.

This invention relates to a condensation apparatus for use with particle counters. More particularly, the invention relates to a condensation apparatus that can increase the effective size of gas-entrained nano-particles so that they can be detected by an optical particle counter.

BACKGROUND OF THE INVENTION

There is currently a great deal of concern about the health effects of nano-particles emitted unintentionally into the air. For example, the 500% increase in respiratory illness and allergies in the UK in recent years has been associated in part with particles emitted by diesel engines and other combustion processes. Whilst the main focus has been on diesel emissions, attention is turning to other potential sources such as power generation using fossil fuels, incineration, nuclear power generation and aircraft emissions. All heavy industries involving processes emitting fumes have potential problems with the emission of nano-particles. Such processes include smelting, firing, glass manufacture, welding, soldering, nuclear power generation and incineration. There is also concern amongst consumer companies that enzymes in washing powders, powder coatings and fibres used in disposable nappies and other products could cause problems. In addition, the US EPA is becoming increasingly concerned about gasoline engine emissions.

Nano-particles are known to produce toxic effects. For example, they can cross the blood-brain barrier in humans and gold nano-particles can move across the placenta from mother to foetus. Early studies with PTFE (polytetrafluoroethylene) particles around 20 nm in diameter showed that airborne concentrations of a supposedly inert insoluble material lower than 50 µg/m³ could be fatal to rats. Moreover, nano-tubes produce a more toxic response in rats than quartz dust.

In addition to concerns from a health perspective, the elimination or control of airborne nano-particles is important in maintaining standards in the many thousands of clean rooms in the micro-electronics, pharmaceutical, medical, laser, and fibre optics industries.

Small particles can be classified as shown in Table 1 below.

TABLE 1

| Term | Aerodynamic Particle Size Range |
| --- | --- |
| Dust | D > 10 µm |
| Coarse particles | 2.5 µm < D < 10 µm |
| Fine particles | 0.1 µm < D < 2.5 µm |
| Nano-particles or ultrafine particles | 1 nm < D < 0.1 µm |

The term "nano-particles" is used to refer to particles having an aerodynamic particle size in the range from 1 nm to 0.1 µm (100 nm).

For spherical particles, the aerodynamic particle size is the diameter of the particle. Real particles in the air often have complicated shapes. For non-spherical particles, the term "diameter" is not strictly applicable. For example, a flake or a fibre has different dimensions in different directions. Particles of identical shape can be composed of different chemical substances and have different densities. The differences in shape and density cause considerable confusion in defining particle size.

The terms "aerodynamic particle size" or "aerodynamic diameter" are therefore used in order to provide a single parameter for describing real non-spherical particles having arbitrary shapes and densities. As used herein, the term "aerodynamic diameter" is the diameter of a spherical particle having a density of 1 g/cm³ that has the same inertial property (terminal settling velocity) in the air (at standard temperature and pressure) as the particle of interest. Inertial sampling instruments such as cascade impactors enable the aerodynamic diameter to be determined. The term "aerodynamic diameter" is convenient for all particles including clusters and aggregates of any forms and density. However, it is not a true geometric size because non-spherical particles usually have a lower terminal settling velocity than spherical particles. Another convenient equivalent diameter is the diffusion diameter or thermodynamic diameter which is defined as a sphere of 1 g/cm³ density that has the same diffusivity as a particle of interest.

The investigation and monitoring of nano-particles in the atmosphere has been hampered by a shortage of instruments which can measure in the nano-particle range but which are sufficiently inexpensive, robust and convenient to be used on a widespread basis.

Some instruments for measuring nano-particles are known which make use of laser optics to detect and measure particles. However, because optical measurements cannot readily be used to detect particles in the nano-particle size range, techniques have been developed for "growing" particles to make them larger and therefore detectable and this technique forms the basis for Condensation Particle Counters. Condensation Particle Counters (CPCs) work by passing a sample of airborne particles through a chamber containing a vapourised liquid and then through a condenser where the vapourised liquid is condensed onto the airborne particles to form droplets of a size that can be measured. One example of such an instrument is disclosed in WO 02/029382 (Ahn et al). The CPC disclosed in WO 02/029382 comprises a cylindrical evaporation chamber which is lined with a porous absorbent support formed from a material such as nonwoven fabric. At one end of the chamber, the porous absorbent support is in contact with a reservoir of a volatile liquid such as isobutanol so that the liquid can travel along and soak the support by capillary action. The exterior surface of the evaporation chamber is surrounded by a heating element that heats the chamber causing isobutanol to evaporate from the support thereby to create a vapour-filled chamber. Air samples suspected of containing airborne particles are introduced into the chamber at the reservoir end and drawn through the chamber into a condenser where the condensation of the isobutanol vapour onto the airborne particles takes place to form droplets that can be measured using an optical particle counter.

An example of a commercially available CPC making use of the principles discloser) in WO 02/029382 is the Model 3025A Ultrafine Condensation Particle Counter available from TSI Incorporated, Shoreview, Minn., U.S.A.

Another known apparatus is the handheld CPC 3007 from TSI (www.tsi.com), and the operation of this is described in more detail below in relation to FIG. 1.

Existing Condensation Particle Counters suffer from a number of disadvantages. For example, they tend to require a high power consumption in order to heat the working fluid and have a long (10 to 20 minutes) warming up time before they can be used. These disadvantages arise at least in part because the evaporation chamber is heated by means of an external heating element and therefore the entire casing surrounding the chamber must heated before the instrument reaches the operating temperature. Furthermore, with known CPCs, there is a relatively high consumption of the working fluid (e.g. isobutanol) with the result that the working fluid must be topped up on a frequent basis, often before each use. Even in the case of the TSI US 3007 handheld condensation particle counter, the working fluid cartridge with the working fluid must be replaced on a regular basis. A further disadvantage of known CPCs is the unpleasant smell of the working fluids used (e.g. iso-butanol) and the relatively high costs.

At present, therefore, there remains a need for a Condensation Particle Counter that can be used for long periods without topping up the working fluid, which has a greatly reduced warm-up time and which lends itself to miniaturisation.

SUMMARY OF THE INVENTION

The present invention sets out to provide a condensation apparatus which, when used in a Condensation Particle Counter, can overcome or at least alleviate some or all of the problems described above in relation to known CPCs.

In a first aspect, the invention provides apparatus for increasing the size of gas-entrained particles in order to render the gas-entrained particles detectable by a particle detector, the apparatus comprising an evaporation chamber and a condenser;

the evaporation chamber having an inlet for admitting gas into the evaporation chamber and an outlet through which vapour-laden gas may leave the evaporation chamber;

the evaporation chamber having disposed therein a heating element and a porous support, the heating element being in direct contact with the porous support, wherein the porous support carries thereon a vaporisable substance and the heating element is heatable to vaporise the vaporisable substance to form vapour within the evaporation chamber;

the condenser being in fluid communication with the outlet of the evaporation chamber, and the condenser having an outlet for connection to the particle detector.

the apparatus being configured so that vapour-laden gas from the evaporation chamber can flow into the condenser and condensation of the vaporisable substance onto gas-entrained particles in the condenser takes place to increase the size of the particles so that they are capable of being detected by a single particle detector.

In one embodiment, the evaporation chamber has at least two inlets, one of which serves to admit a sample gas containing gas-entrained particles into the evaporation chamber and another of which is connectable to a source of substantially particle-free carrier gas.

In another embodiment, the condenser has at least two inlets, one inlet being in fluid communication with the evaporation chamber and another inlet serving to admit a sample gas containing gas-entrained particles into the condenser.

In a second aspect of the invention, there is provided apparatus for increasing the size of gas-entrained particles in order to render the gas-entrained particles detectable by a particle detector, the apparatus comprising:

a source of a vaporisable substance;

heating means to bring about evaporation of the vaporisable substance to form vapour;

an inlet for admitting a sample gas containing gas-entrained particles;

a condenser, the condenser being provided with an outlet for connection to the particle detector;

the apparatus being configured such that condensation of the vapour onto gas-entrained particles takes place in the condenser to increase the size of the particles so that they are capable of being detected by the particle detector;

characterised in that the vaporisable substance is selected from dimethyl phthalate, dioctyl phthalate and dimethylsulphoxide.

In a further aspect, the invention provides a condensation apparatus for increasing the size of gas-entrained particles in order to render the gas-entrained particles detectable by a particle detector, the apparatus comprising:

an evaporation chamber;

a condenser in fluid communication with the evaporation chamber and having an outlet for connection to a particle detector;

a heating element and a porous support each disposed within the evaporation chamber, the porous support carrying thereon a vaporisable substance and the heating element being heatable to vaporise the vaporisable substance to form vapour within the evaporation chamber;

a first inlet for admitting a stream of carrier gas into the evaporation chamber to carry vapour through to the condenser;

a second inlet which is downstream of the porous support and through which a stream of sample gas containing gas-entrained particle can be introduced;

the apparatus being configured so that condensation of the vaporisable substance onto the gas-entrained particles in the sample gas takes place in the condenser to increase the size of the particles so that they are capable of being detected by a particle detector.

As described above in the introductory section of this application, many particle counters, particularly those based on optical methods of particle detection, are unable efficiently to detect and count particles having a particle diameter of less than about 300 nm. The condensation apparatus of the invention enables particles of much smaller size (e.g. an aerodynamic particle diameter down to less than 3 nm) to be detected and achieves this by growing the particles by condensing onto them a vaporisable condensable substance.

The vaporisable substance can be a liquid or a vaporisable solid. Where the vaporisable substance is a solid at room temperature, it is preferably one that melts first to form a liquid and then forms a vapour from the liquid state rather than a substance that sublimes from the solid state.

Examples of solid materials that can be used as the vaporisable substance include solid hydrocarbons and long chain carboxylic acids, e.g. fatty acids such as stearic acid.

It is currently preferred, however, that the vaporisable substance is a liquid.

Liquids that may be used include water and alcohols such as propanol, isopropanol and isobutanol, or higher boiling organic liquids. As discussed above in the introduction, one of the disadvantages of known condensation particle counters is that liquid used as the vaporisable substance is consumed within a relatively short period of time and therefore fresh liquid must be added at frequent intervals. With some known condensation particle counters, it is necessary to add more liquid each time the apparatus is used.

In order to overcome the disadvantages associated with known condensation particle counters, it is preferred to use as the vaporisable substance a liquid having a boiling point at atmospheric pressure of at least 110° C.

One group of preferred vaporisable liquids consists of dimethyl phthalate, dioctyl phthalate and dimethylsulphoxide. One particularly preferred liquid is dimethyl phthalate. By using higher boiling liquids such as dimethyl phthalate, the rate of consumption of the liquid is greatly reduced and hence the liquid does not need to be topped up so frequently.

Where the vaporisable substance is a liquid and the evaporation chamber contains or is linked to a reservoir of liquid, there is a possibility that tipping the apparatus (e.g. while in transit) could cause liquid to leak into any inlets or outlets of the evaporation chamber. In order to prevent or minimise the likelihood of this occurring, the inlet(s) and outlet(s) of the evaporator chamber can be provided with a lip or rim which acts as a barrier to liquid. It will be appreciated that the height of the rim or lip will depend upon the volume of liquid carried in the reservoir. The lip or rim may be defined or provided by the end of an inlet or outlet tube extending into the evaporation chamber. By way of example, the rim or lip may be from 1 to 8 mm high, more preferably 2 to 5 mm high.

The carrier gas may be air or a pure gas or mixture of gases. For example, instead of air, the carrier gas could be nitrogen gas. The carrier gas is preferably filtered so that particles and other impurities are not carried through the evaporation chamber into the condenser. The carrier gas can be provided from a particle-free source, for example a cylinder of gas. Alternatively or additionally, a filter can be located externally of the evaporation chamber. For example, a filter can be located across the first inlet itself, or a filter can be located upstream of the first inlet, so that, in either case, carrier gas entering the evaporation chamber is free from impurities and especially particulate impurities. Examples of filters include HEPA filters and such filters are well known and do not need to be described in detail here.

In an alternative arrangement, the carrier gas can be filtered after it has entered the evaporation chamber. For example, in one embodiment, a filter can consist of or comprise the porous support for the vaporisable substance. In this embodiment, the porous support acts as a filter membrane that extends across the interior of the evaporation chamber dividing it into an upstream compartment and a downstream compartment. Carrier gas entering the upstream compartment through the first inlet may contain particulate impurities which are removed as the carrier gas passes through the porous support, whilst at the same time the vaporisable substance on the porous support is evaporated and the vapour is carried off by the filtered carrier gas. Thus, on the downstream side of the porous support, there are no particulate impurities present. It will be appreciated that by "particulate impurities" is meant particles other than those that are intended to be detected and counted.

The porous support can take various forms and be made from any of a number of different materials. For example, the porous support can be formed from a porous ceramic material or a porous fabric such as glass cloth, quartz fibre filter rockwool or a cotton fabric. The porous material should be stable at the temperatures used to vaporise the vaporisable substance and, when the vaporisable substance is a liquid, should preferably be wettable by the substance.

A temperature sensor e.g. a thermocouple) is typically disposed within the evaporation chamber for sensing the temperature inside the chamber interior. The temperature sensor is preferably in thermal contact with or in close proximity to the heating element. The temperature sensor may be arranged so that it is encircled by the heating element and/or the porous support. The temperature sensor is typically connected to a temperature control device.

The heating element can take various forms but, in each case, the heating element is disposed inside the evaporation chamber and is in close proximity to the porous support rather than surrounding the exterior of the chamber (as is the case in known commercially available condensation particle counters). A significant advantage in placing the heating element inside the evaporation chamber is that it greatly reduces the warm-up time of the instrument and the power consumption of the instrument. Thus, CPCs containing the condensation chambers of the invention can be warmed up to operating temperature in under a minute in contrast to the 10-20 minutes required for known CPCs to reach operating temperatures.

Most preferably the heating element is in direct contact with the porous support.

For example, the porous support can surround the heating element.

In one embodiment, the heating element comprises a rod (e.g. cylindrical rod) portion and the porous support surrounds the said rod (e.g. cylindrical rod) portion. For example, the porous support can comprise a sleeve that fits over the rod (e.g. cylindrical rod) portion of the heating element. Such a form of construction is particularly suitable for use when the porous support is formed from a porous fabric as hereinbefore defined.

The porous support (e.g. sleeve) may have a downwardly depending portion which, in use, extends into a reservoir of the vaporisable substance (when a liquid).

The rod portion of the heating element can have a hollow interior within which is disposed a heater wire or heater probe and optionally a thermocouple. In order to ensure good thermal contact between the heater wire or heater probe and the inner surface of the hollow rod, a thermally conductive filler may be used to hold the heater wire or heater probe and the thermocouple (when present) in place. Examples of thermally conductive fillers include solders and other low melting alloys, and thermally conducting resins such as metal particle-filled resins (e.g. epoxy resins).

Vaporising-devices incorporating heating elements of the aforesaid type are believed to be new and represent a further aspect of the invention. Accordingly, in another aspect, there is provided a vaporiser device for use in a condensation particle counter, the vaporiser device comprising:

a heating element comprising a mounting portion for installing in a wall of an evaporation chamber in the condensation particle counter, and a rod portion; the rod portion being arranged to extend inwardly into the evaporation chamber in use; and a porous support which surrounds and is in contact with the rod portion, the porous support carrying or being capable of carrying a vaporisable substance;

and optionally retaining means for holding the porous support in place on the rod portion.

The rod portion of the heating element and the porous support may be as defined above.

The retaining means can comprise or consist of a clip or perforated sleeve that fits over the porous support to hold it in place.

The evaporation chamber may vary in cross sectional shape and can be, for example, of circular or rectangular cross section.

The apparatus of the invention may be provided with a second inlet through which is introduced a stream of sample gas containing the gas-entrained particles to be counted. The second inlet can be disposed so that it opens into the evaporation chamber, or into an intermediate chamber between the evaporation chamber and the condenser, or into the condenser.

In one embodiment, the second inlet is arranged so that it opens into the evaporation chamber. The second inlet may have a nozzle that extends into the evaporation chamber. When the second inlet is located in the evaporation chamber, it is preferably in-line with an exit opening communicating with the condenser, e.g. so that a longitudinal axis of the inlet is aligned with a longitudinal axis of the condenser. The second inlet preferably has a cross sectional area less than the cross sectional area of the exit opening; e.g. the second inlet when circular has a diameter less than the diameter (when circular) of the exit opening. In this embodiment, without wishing to be bound by any theory, it is believed that a stream or jet of the sample gas is surrounded by a concentric layer of carrier gas and vapour as it leaves the evaporation chamber, mixing of the two concentric layers taking place as they move along the condenser.

In another embodiment, the second inlet is arranged so that it opens into the condenser. Preferably, an exit opening of the evaporation chamber is provided with a nozzle that extends into the condenser to a position level with or downstream of the second inlet. With this arrangement, without wishing to be bound by any theory, it is believed that a stream of carrier gas and vapour from the evaporation chamber is surrounded by a concentric layer of sample gas as it enters the condenser, mixing of the two concentric layers taking place as they move along the condenser.

Where the second inlet opens into the condenser, the sample gas may be partially or wholly saturated with vapour before it enters the condenser. In this embodiment, the second inlet may be connected to an ancillary evaporation chamber.

In a further embodiment, the apparatus is configured such that:
 the second inlet is arranged so that it opens into an intermediate chamber between the evaporation chamber and the condenser;
 the intermediate chamber is divided by a dividing wall into upstream and downstream sub-chambers, a central hole in the wall providing communication between the sub-chambers, whereby the second inlet opens into the upstream sub-chamber;
 a third inlet opens into the downstream sub-chamber, the third inlet being connectable to a supply of filtered gas;
 a nozzle is provided that extends from an exit opening of the evaporation chamber into the condenser to a position in the upstream sub-chamber that is level with or downstream of the second inlet;
 the downstream sub-chamber contains a cylindrical baffle that is aligned with the said nozzle and the central hole in the dividing wall, and the third nozzle opens into a space surrounding the cylindrical baffle.

With the foregoing arrangement, without wishing to be bound by any theory, it is believed that a stream of carrier gas and vapour from the evaporation chamber is surrounded by a concentric layer of sample gas as it exits the nozzle into the upstream intermediate sub-chamber. As the two concentric layers of carrier gas/vapour and sample gas pass through the central hole in the dividing wall into the downstream intermediate chamber, they are surrounded by a further concentric layer of filtered carrier gas entering through the third inlet. Thus there is formed, temporarily, a tri-laminar stream of gas consisting of a central core of carrier gas and vapour, an intermediate layer of sample gas containing gas-entrained particles, and an outer layer of filtered carrier gas. The tri-laminar stream of gas then exits the intermediate chamber through the interior of the cylindrical baffle and into the condenser where mixing of the three layers occurs.

In each of the foregoing embodiments, as the mixture of heated carrier gas, sample gas, gas-entrained particles and vapour passes along the condenser, cooling leads to the gases within the condenser becoming supersaturated with the vapour of the vaporisable substance with the result that it condenses onto the surface of the particles. When the vaporisable substance is a liquid, droplets are formed on or around the particles, whereas when the vaporisable substance is a normally a solid at room temperature, cooling leads to the formation of beads containing or bearing the particles. In this way, the size of the particles is effectively increased from sizes as low as 3 nm to sizes up to and in excess of 1 μm. By increasing the size of the particles, they are rendered detectable by optical particle detectors such as optical particle counters.

The condenser is typically formed from a material of high thermal conductivity and is made sufficiently long to ensure that the mixture of carrier gas, sample gas, vapour and particles to be detected cools sufficiently to allow the vaporisable substance to condense onto the particles to grow the particles to a detectable size (e.g. 1 μm or greater). The condenser can therefore take the form of a tube formed from a metal material such as aluminium or stainless steel. The thickness of the walls of the condenser and other parts of the apparatus can be as thin as practical, but, when there is an intention to use the apparatus under elevated or reduced pressure (e.g. at 10 bar), the wall should be sufficiently thick to withstand such pressures.

In order to assist cooling of the mixture of gases, vapour and particles in the condenser, cooling means may be provided.

In one embodiment, the cooling means comprises one or more fans each directing a flow of air onto the external surface of the condenser. In one embodiment there is one fan. In another embodiment there are two fans.

The fan(s) may or may not be part of an air temperature controlling system. The temperature controlling system enables the air cooling the condenser surface to be maintained at a pre-set temperature which is not influenced by the temperature of the air surrounding the condensation chamber.

Alternatively, a cooling element may be located in contact with the external surface of the condenser. The cooling element can be, for example, a thermoelectric cooling device (e.g. a Peltier cooling device).

In order to facilitate improved cooling, the cross-section of the condenser may be formed in such a way as to enhance the ratio of the circumference to cross-section area.

The condenser preferably has a surface area to volume ratio which is greater than the surface area to volume ratio of a cylinder. By increasing the surface area to volume ratio, the condenser can be made more efficient resulting in more rapid cooling and thereby enabling the size of the condenser to be reduced.

A condenser can be defined as having a length (a dimension corresponding to the distance between the inlet and outlet of the condenser), a width (a dimension orthogonal to the length) and a height (a dimension orthogonal to the length and height). In the case of a tubular condenser of circular cross section, the width and the height are the same and both correspond to the diameter of the tube. In the case of a rectangular condenser of square cross section, the width and height are also the same. However, in this application, where the width and height of a condenser are not the same, the reference to "height" means the lesser of the two dimensions.

The surface area to volume ratio of a condenser can be increased in a number of ways. For example, at least part of the condenser may have a portion of flattened cross section or may be have an elongate oval or rectangular shape in cross section, i.e. a cross section in which the height is substantially less than the width of the condenser. In one preferred embodiment, the condenser is substantially rectangular in cross section wherein the height is less than half the width.

In another embodiment, the condenser may comprise an annular or part annular condenser body. An annular condenser body may be formed from two concentric cylinders with the hot vapour laden gas being directed through the annular space between the inner and outer cylinders and cooling air being directed through the interior of the inner cylinder as well as around or against the outer surface of the outer cylinder.

In order to enable particle sizes to be measured accurately, it is important to ensure that the residence time of each particle in the condenser is substantially the same. This means that the flow velocities and flow paths of the particles through the condenser should ideally be as uniform as possible.

Where a non-cylindrical condenser (e.g. a rectangular condenser) is connected to in-line cylindrical inlets and outlets, there exists the possibility of non-uniform flow between the inlet and outlet, particularly in cases where the width (as defined herein) of the condenser is greater than the diameters of the inlet and outlet. In order to overcome this potential problem, a condenser (e.g. a substantially rectangular condenser) may be provided with a pair of flow distributor tubes which are aligned substantially at right angles with respect to the length (direction of flow) of the condenser. The flow distributor tubes are connected to the inlet and outlet of the condenser and each extend across the width of the condenser and are provided with elongate slots or arrays of holes which open into the interior of the condenser.

Accordingly, in another aspect of the invention, there is provided a condenser for use with an apparatus of the invention as defined herein, the condenser comprising:

a condenser body having an inlet, an outlet and a hollow interior which has an internal length, an internal width and an internal height;

an inlet flow distributor tube connected to the inlet of the condenser body and extending across the internal width of the condenser body; and an outlet flow distributor tube connected to the outlet of the condenser body and extending across the internal width of the condenser body;

wherein the internal height of the condenser body is less than a corresponding internal height of each of the inlet and outlet flow distributor tubes;

inlet and outlet flow distributor tubes each being provided in the walls thereof with one or more slots or holes communicating with the hollow interior of the condenser body so as to provide a flow path from the inlet flow distributor tube through the hollow interior of the condenser and into the outlet flow distributor tube.

The inlet flow distributor tube in use is attached or otherwise in fluid communication with the outlet of the evaporation chamber whereas the outlet flow distributor tube is attached or otherwise in fluid communication with the particle detector.

The configuration of the flow distributor tubes, and the positioning of the slots or holes, is such as to provide a substantially uniform flow of gas through the condenser body to the particle detector.

The flow distributor tubes may be, for example, of circular cross section, oval cross section or polygonal (regular or irregular) cross section. In one embodiment, the flow distributor tubes are of circular cross section.

The internal cross sectional area of each flow distributor tube is preferably greater than the internal cross sectional area (internal width×internal height) of the condenser body. As an example, if the cross-section of the flow distributors is a circle of internal diameter Dt and the condenser internal height is Hc and the internal width We then $\pi Dt^2>Hc*Wc$. The ratio of $\pi Dt^2/(Hc*Wc)$ should typically be more than 1.1 or preferably more than 2 or even more preferably the ratio should be more than 3.

As indicated above, fluid communication between the interiors of the flow distributors 102 and 104 and the interior of the rectangular condenser may be achieved by providing the walls of the flow distributor tubes with elongate narrow slots or an array (preferably linear) of holes that open into the hollow interior of the condenser body. Preferably fluid communication between the flow distributor tubes and the interior of the condenser body is provided by means of a narrow slot in the wall of each flow distributor tube. By making the slots narrow, the internal diameters of the flow distributor tubes can be reduced because the uniformity of the flow in the condenser is governed by the ratio of the internal height (Hc) of the condenser to the width (Ws) of the slot. In the present context, the width of the slot means the dimension which is in the same direction as the internal height of the condenser (in contradistinction to the "length" of the slot where the reference to "length" the dimension which is in the same direction as the internal width of the condenser). Typically, the ratio of Hc/Wc should be more than 1.1 or preferably more than 2 or even more preferably the ratio should be more than 3.

In another embodiment, the walls of the flow distributor tubes contain holes evenly distributed along the inlet and outlet of the rectangular condenser 103 instead of slots. The number of holes Nh should be more than 1 or preferably more than 4 or even more preferably more than 10. The diameter of the holes Dh should be sufficiently small and can be evaluated from the expression: $\pi Dt^2>Nh*\pi Dh^2$. The ratio of $\pi Dt^2/(Nh*\pi Dh^2)$ should be more than 1.1 or preferably more than 2 or even more preferably the ratio should be more than 3.

The flow distributor tubes can be made from any of a variety of materials. For example, they can be made from stainless steel tube, PTFE, aluminium, or any suitable metal, glass, ceramic or plastics material. The condenser body is preferably made from a heat conducting material such as a metal, e.g. a steel such as a stainless steel.

One potential problem with the condensers, especially when they have a small internal cross sectional area or width (e.g. less than 2 mm), is that condensation on the walls of the condenser can lead to blockage. In order to overcome this problem, means may be provided for removing condensed substance from the interior walls of the condenser. For example, the condenser may have one or more drainage ducts extending along all or part of its length, the drainage ducts being separated from the interior of the condenser by a semi-permeable wall or membrane through which the liquid condensate can pass, the drainage ducts having one or more outlets connectable to a pump to extract liquid condensate from the ducts. The semi-permeable membranes are constantly filled with the working fluid and therefore the gas flow cannot penetrate through them. By means of such an arrangement, when the vaporisable substance condenses on the inner wall of the condenser, rather than accumulating in and blocking the condenser, it is extracted through the semi-permeable wall into the drainage ducts and away from the condenser interior. Once extracted, the condensate can either be sent to a waste storage compartment for later disposal or recycled back to the evaporation chamber.

The ducts can be formed by partitioning the interior of the condenser over at least part of its length by means of one or more longitudinally extending semi-permeable walls or membranes. The semi-permeable walls or membranes may be provided with capillaries that draw condensate from the interior of the condenser into the drainage ducts. For example, the walls or membranes can be formed from a ceramic or stainless steel filter material having a capillary size of <0.5 mm, e.g. 1-10 μm.

The condensation apparatus of the invention is designed to be connected to a particle detector, typically a particle detector capable of single particle detection and/or single particle counting.

More typically, the condensation apparatus of the invention is designed to form part of a Condensation Particle Counter and, for this purpose, can be connected to a particle counter which can be, for example, a Naneum 'SAC 1' particle counter available from Naneum Limited of Canterbury, United Kingdom.

Accordingly, in another aspect, the invention provides a condensation particle counter comprising a condensation apparatus of the invention as defined herein.

In another aspect, the invention provides a method of detecting and counting nano-particles using a condensation particle counter comprising a condensation apparatus of the invention as defined herein.

Further aspects and features of the invention will be apparent from the specific embodiments described below and illustrated in FIGS. 2 to 12.

DETAILED DESCRIPTION OF THE INVENTION

The invention will now be illustrated in greater detail by reference to the specific embodiments described in the following non-limiting examples.

Figure 1:
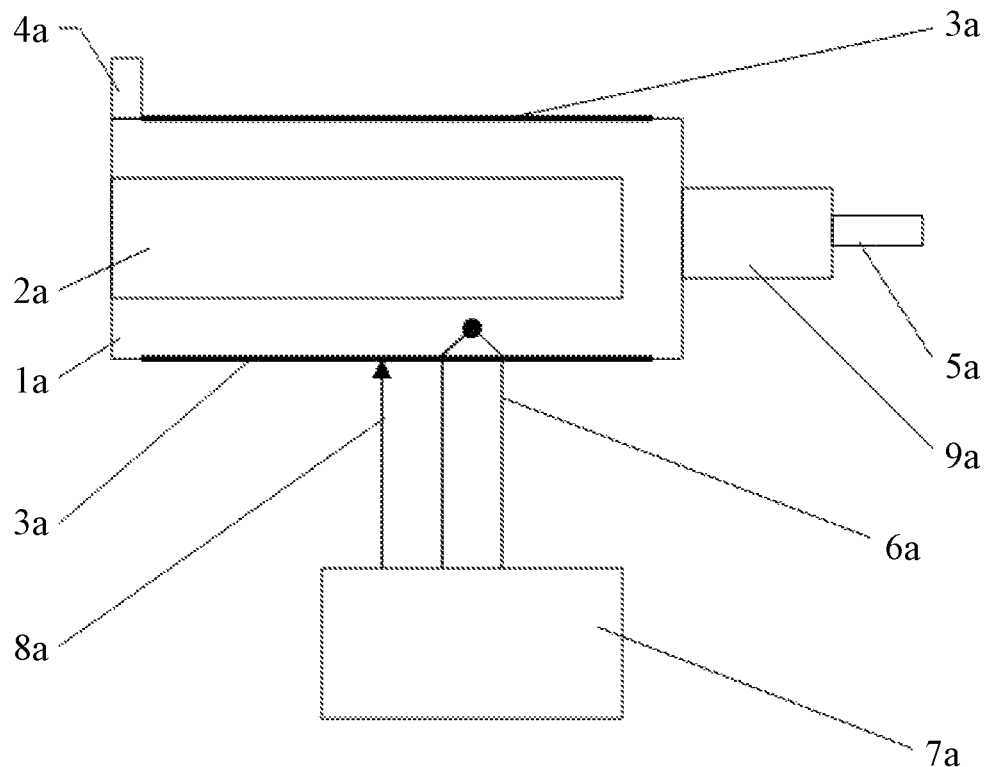
FIG. 1 is a schematic side sectional view of a known type of condensation apparatus.

FIG. 1 is a schematic side sectional view of a known type of condensation apparatus that can be used in combination with a particle counter. One such known condensation apparatus is the apparatus found in the handheld CPC 30007 from TSI (www.tsi.com). The apparatus comprises an evaporation chamber $1a$ with a porous support in the form of a cartridge $2a$ soaked in a volatile working fluid. The chamber $1a$ has a cylindrical shape and an internal diameter that is greater than the external diameter of the cartridge $2a$. The evaporation chamber $1a$ is provided with an inlet $4a$ and outlet $5a$, and a heating element $3a$, which encircles the outer wall of the chamber. The temperature of the chamber is measured by a sensor $6a$ and controlled by a control unit $7a$ using interface $8a$ connected to the heating element on the outer wall of the chamber. A condenser $9a$ is placed between the chamber $1a$ and the outlet $5a$.

A stream of air containing small gas-entrained particles (e.g. airborne particles) is drawn into the chamber $1a$ via inlet 4a by means of a pump (not shown). As it passes through the evaporation chamber, the stream of air is heated and saturated with vapour formed by evaporation of the working fluid. The vapour-saturated stream of air then passes into the condenser where cooling of the air and condensation of the working fluid onto airborne particles takes place. As a result, the particles grow by condensation up to a readily detectable size of about 1 μm.

The enlarged particles pass out through the outlet 5a, and are directed to an optical particle counter where they are counted.

The condensation apparatus illustrated in FIG. 1 can be used to detect and count particles in the size range from 10 nm to 600 nm. However, the apparatus suffers from a number of disadvantages.

One major disadvantage is that the working fluid must be replaced on a regular and frequent basis.

A further disadvantage is that the apparatus is very slow to warm up to an operating state. In the case of the TSI CPC 3007 described above, the apparatus has a 600 second warming up time before it can be used.

Another disadvantage is that the layout of the apparatus does not readily lend itself to miniaturisation. Reducing the size of the apparatus would necessitate using a smaller working fluid cartridge which would therefore need to be refilled more frequently. Thus, miniaturisation would lead to a reduction in the period of time over which the apparatus could be used without refilling.

A further disadvantage is that the abovementioned TSI CPC 3007 instrument cannot be used in an environment of elevated pressure and, according to its product specification, the instrument will only operate when held horizontally.

The relatively rapid depletion of working fluid in the cartridge in the CPC shown in FIG. 1 affects the performance of the condensation unit because it leads to a lower concentration of vapour of the working fluid in the air inside the chamber. When the vapour concentration is lower, vapour tends to condense preferentially on relatively large particles and therefore the smaller particles are not detected and counted. For instance, the lower detection limit can increase by as much as 10 nm to 15 or 20 nm due to working fluid depletion. Since it is very difficult to monitor the extent or rate of depletion in practice, there is a chance that many small particles will not be detected and counted.

The condensation apparatus of the invention overcomes or at least alleviates the problems identified above with known CPCs.

Figure 2:
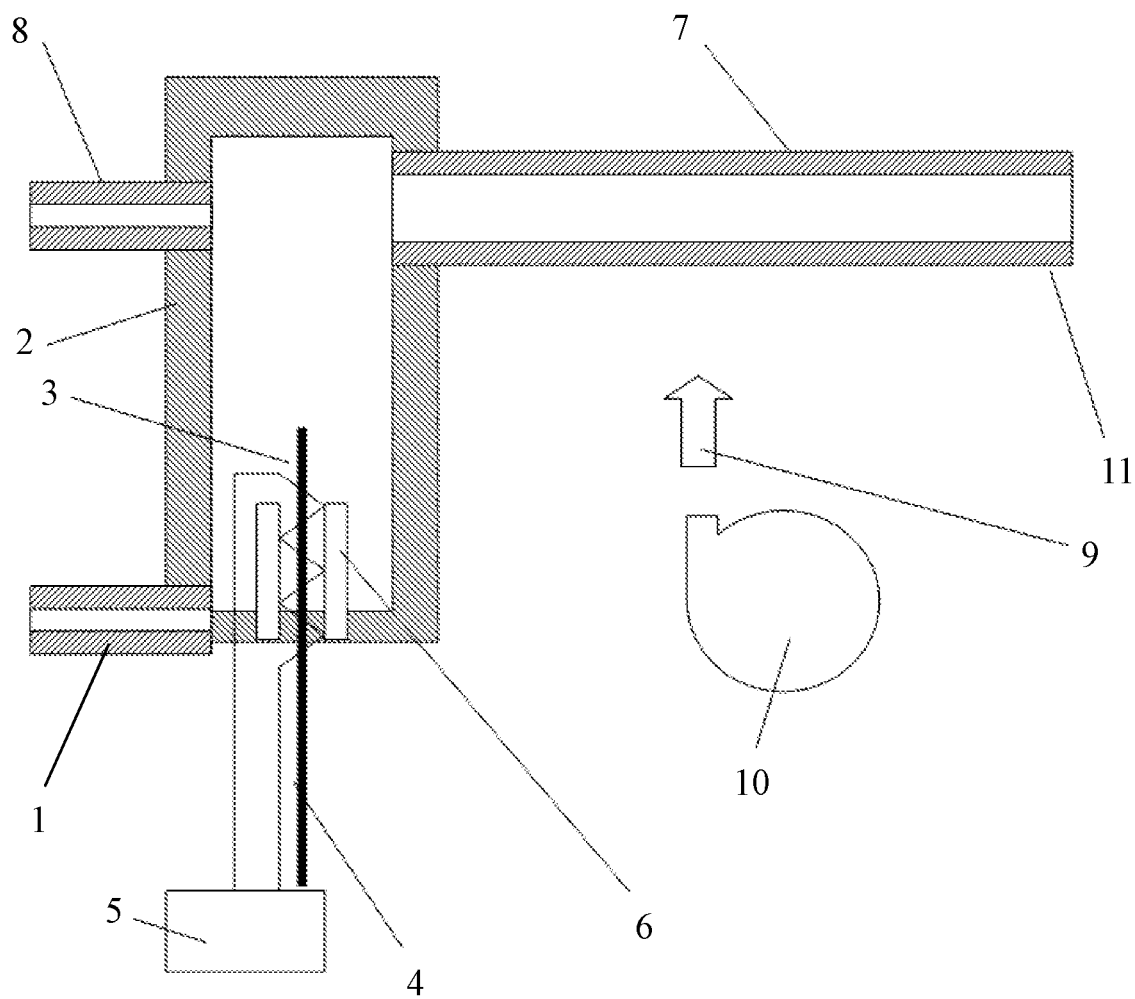
FIG. 2 is a schematic view of a condensation apparatus according to a first embodiment of the invention.

A condensation apparatus according to a first embodiment of the invention is shown in FIG. 2. The apparatus comprises:

An evaporation chamber 2 with one inlet 1 (the "first inlet") for a clean gaseous medium, e.g. a clean air where all relevant aerosol particles have been removed.

Another inlet 8 (the "second inlet") through which a stream of a sample gas (e.g. air) containing nano-particles of interest can be drawn into the evaporation chamber. The inlet 8 is positioned at a distance from the first inlet, e.g. at the top of the chamber while the first inlet 1 is positioned at the bottom of the chamber.

A heating element 3 which is in sufficiently close thermal contact with a temperature sensor 4, the element being covered by a porous support 6 wettable by the working fluid. The porous support 6 is soaked with a working fluid of low equilibrium vapour pressure, for instance a semi-volatile organic compound such as dimethyl phthalate.

A temperature controlling device 5 that keeps the temperature of the surface of the porous support 6 at a level sustaining formation of a sufficient high vapour density of the working fluid;

A condenser/outlet 7 made of a material of high thermal conductivity and sufficiently long to let droplets of the working fluid be formed on nano-particles of interest and to grow to a size that enables them to be detected and counted by means of single particle counting. The condenser/outlet 7 is positioned near or opposite the second inlet 8 to provide effective mixing of the carrier gas and sample gas streams entering the chamber through the first and the second inlets. The condenser/outlet 7 is positioned in line with the second inlet.

A temperature cooling device 10 that keeps the temperature of the surface of the condenser/outlet 7 at a level sustaining formation and growth of the working fluid droplets. The cooling device 10 is placed in a position that enables effective cooling of the condenser/outlet 7 to be sustained.

In use, a stream of clean carrier gas (e.g. air) which has been filtered through a filter (not shown) and which contains no (or negligible quantities of) detectable aerosol particles enters through inlet 1 into the evaporation chamber 2. In the evaporation chamber, heating element 3 is positioned to be in a good thermal contact with temperature sensor 4 and a predetermined temperature that is sufficient to evaporate working fluid and to generate conditions necessary to sustain condensation of the working fluid on particles of interest is controlled by temperature control device 5 which is linked to the temperature sensor. The working fluid is contained in a porous support that takes the form of a cover 6 that is placed on the heating element 3. In the case of a cylindrical heating element, the cover will be wrapped around its surface and soaked with the working fluid. As a result, the stream of clean air introduced via the inlet 1 is saturated with the vapour of the working fluid and moved towards the condenser/outlet 7. A gas (e.g. air) sample containing nano-particles of interest is introduced into the chamber through the second inlet 8. In the zone between the inlet 8 and the opening into the condenser 7, supersaturation of the working fluid vapours arises due to mixing of the hot saturated vapour and the unheated stream of sample gas containing the nano-particles of interest. Therefore, in this zone, heterogeneous nucleation of the working fluid on the particles of interest begins to occur. When the mixture of vapour and sample gas containing the nano-particles enters the condenser 7, additional supersaturation occurs due to cooling of the gases and vapour by the walls of the condenser/outlet. The excess of heat is removed from the surface of the condenser/outlet 7 by means of a cooling system 10. In FIG. 2 a flow of cold air 9 generated by a blower is shown. In the condenser/outlet droplets of the working fluid grow on the nano-particles up to detectable sizes for instance 1 μm. These droplets can be counted for instance using an optical particle counter (not shown) that is connected to the exit of the chamber 11. Therefore every nano-particle of interest is detected individually.

As an example of the apparatus of shown in FIG. 2, a miniature cylindrical condensation chamber of 10 mm ID was built from PTFE with inlets 1 and 8 made from stainless steel tube of 4 mm OD and a condenser/outlet 7 made from 8 mm OD stainless steel tube. A K-type thermocouple was utilised as a temperature sensor 4. The heater 3 used was a NiCr heater covered by a layer of porous $SiO_2$ soaked with dimethyl phthalate. Particles were counted using a MetOne laser particle counter (Hach ULTRA Analytics).

The temperature was controlled by a Digitron Temperature controller 5. It was found that the condensation apparatus thus constructed was able to enlarge nano-particles up to 1 to 2 μm diameter. The condensation apparatus was used over a period of at least 2 months without refilling.

Figure 3:
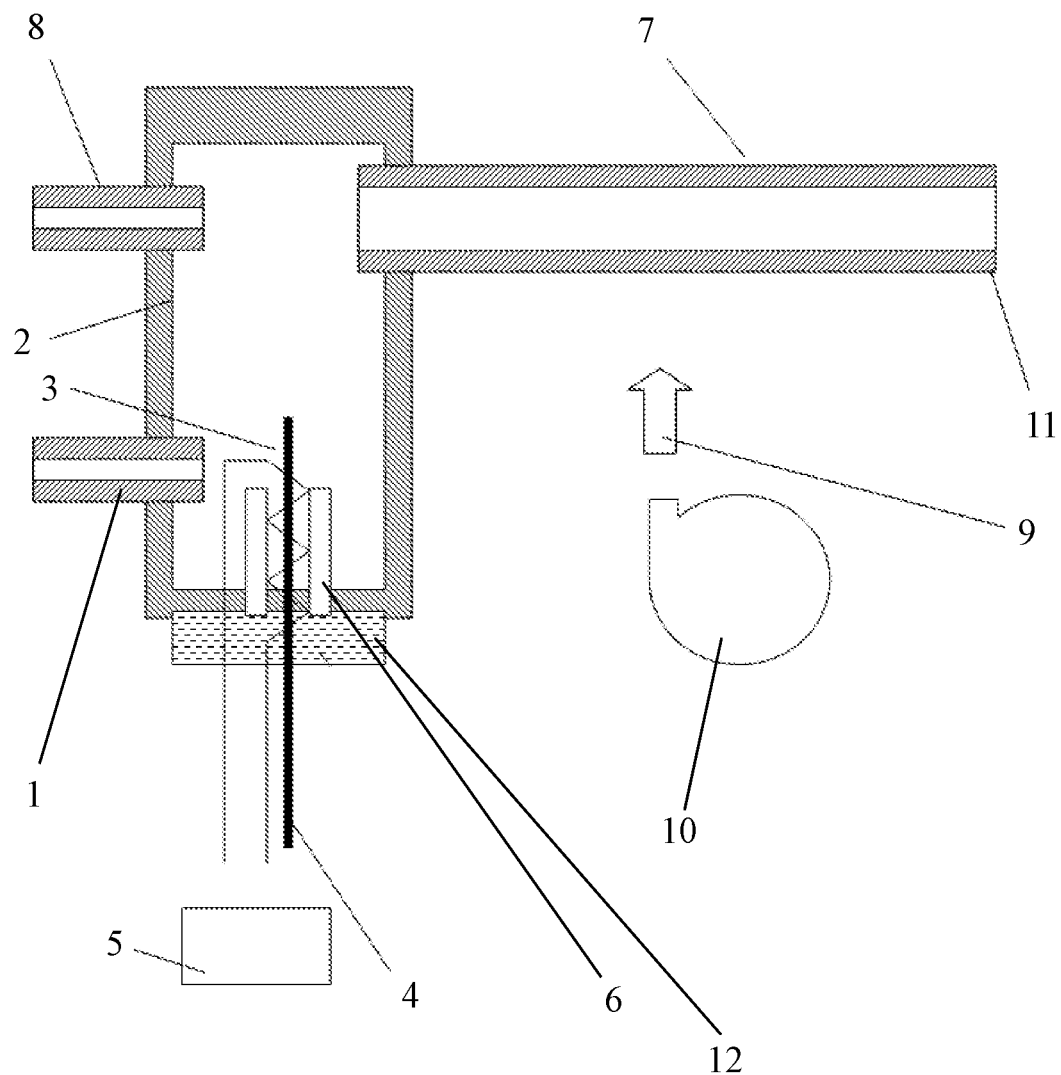
FIG. 3 is a schematic view of a condensation apparatus according to a second embodiment of the invention.

Another embodiment of the present invention is shown in FIG. 3. The apparatus of FIG. 3 is similar to the apparatus of FIG. 2 except that a reservoir 12 of working fluid is provided to extend the period of time over which the apparatus can be operated without refilling. In order to prevent the fluid from the reservoir 12 from escaping and interfering with the condensation process when the apparatus is not in a horizontal position, the inlets 1 and 8 and the condenser/outlet 7 are arranged so that they extend inwardly into the condensation chamber 2. The extensions prevent the escape of working fluid through the inlets 1 and 8 and outlet 7. A condensation apparatus of the type depicted in FIG. 3 has been shown to work for at least 12 months without refilling.

The mode of action of this embodiment is the same as for the embodiment of FIG. 2 above.

Figure 4:
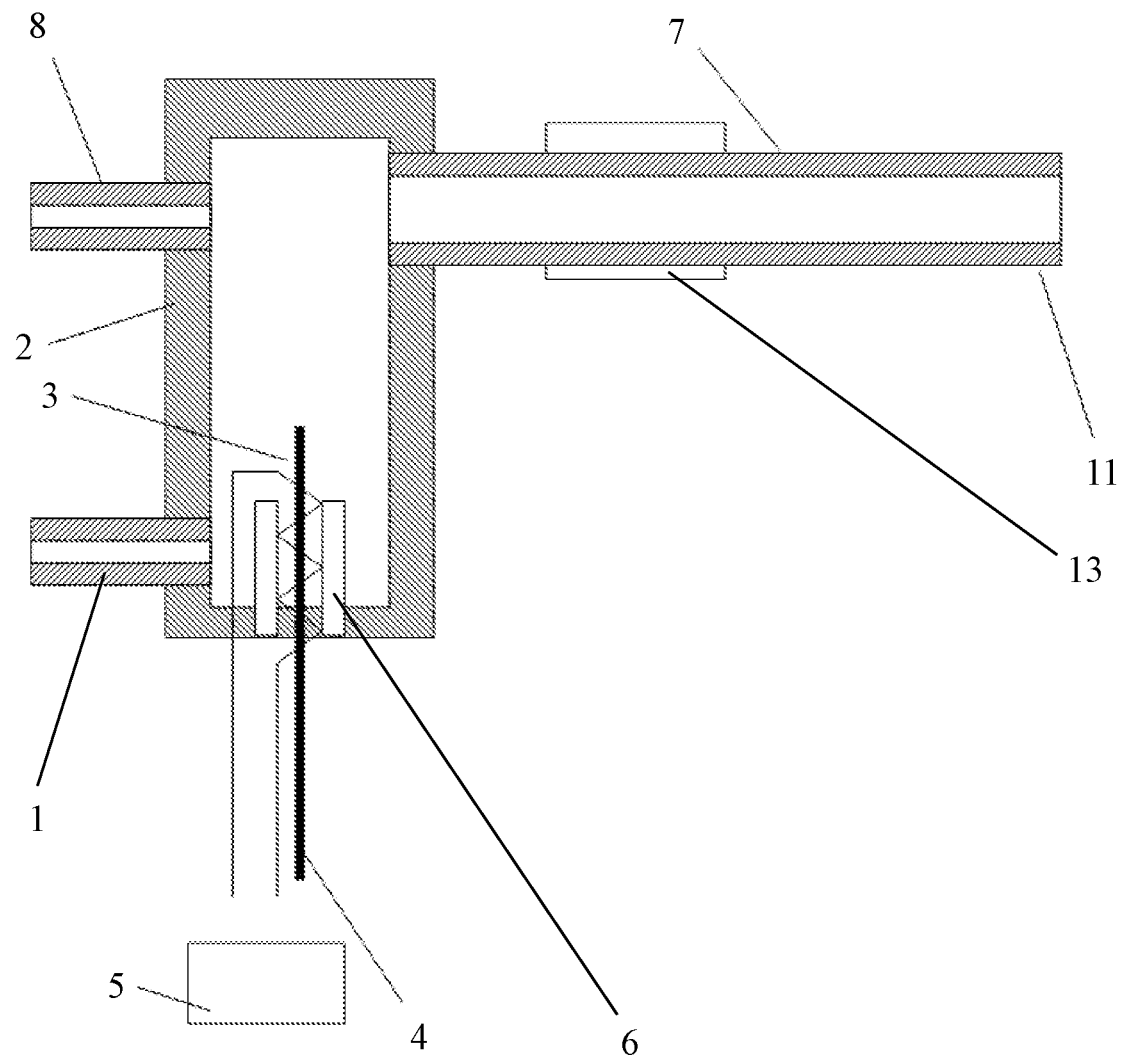
FIG. 4 is a schematic view of a condensation apparatus according to a third embodiment of the invention.

A further embodiment of the invention is illustrated in FIG. 4. In this embodiment, which is similar in construction to the apparatus of FIG. 2, a cooling element 13 is provided which is in thermal contact with the condenser/outlet. The cooling element 13, which can be, for example, a thermoelectric cooling element, is attached to the surface of the condenser/outlet. The cooling element 13 enables heat to be removed from the condenser/outlet in a more efficient manner than is possible with a fan. The enhanced cooling effect of the cooling element 13 increases supersaturation of the vapour within the condenser and enables droplets of the working fluid to grow more rapidly. The operation of the cooling element 13 can be controlled by so that the temperature of the surface of condenser/outlet 7 is lower than the ambient temperature, and therefore the apparatus can be used effectively over a range of ambient temperatures including hot environments. The performance of this embodiment is not influenced by ambient temperature variations.

The shape of the condenser/outlet 7 can affect its performance. In the embodiment shown in FIG. 5, the condenser/outlet 7 has a rectangular cross-section, illustrated by the element labelled as 14. In this embodiment, the cross-section 14 refers to the middle region of the condenser/outlet 7. To either side of the middle region, the condenser can be of any cross sectional shape, e.g. circular. The rectangular cross sectional shape presents a greater surface area onto which the stream of cooling air 9 from the fan 10 can be directed thereby enhancing the efficiency of the cooling of the condenser/outlet 7 which in turn assists the supersaturation of the vapour in the condenser/outlet 7 and improves the efficiency of droplet growth. Although the condenser/outlet 7 is shown as having a middle region of a flat sided rectangular cross section, the shorter sides of the rectangle can be rounded instead of flat so that the cross section is in the shape of an elongated oval rather than a regular rectangle. An elongated oval cross section can be created by the simple expedient of flattening a portion of the tube from which the condenser/outlet 7 is made.

The second inlet 8 can also have a rectangular or elongated oval cross sectional shape. In practice, the ratio of the height to the width of the rectangle can be from 1 to 100.

In each of the embodiments shown in FIGS. 2 to 5, the second inlet 8 is positioned in line with the condenser/outlet and the cross sectional area of the interior of the inlet 8 is less than the cross sectional area of the interior of the condenser/outlet 7. Without wishing to be bound by any theory, it is believed that this arrangement results in the stream of sample gas (e.g. air) containing the aerosol particles being injected into the centre of a stream of vapour and carrier gas so that the mixture entering the condenser/outlet 7 outlet consists of a core stream of sample gas containing the nano-particles surrounded by a sheath of carrier gas and vapour. Mixing between the concentric layers takes place as gases and vapours move along the condenser/outlet 7.

The cross sectional shape of the main body of the condensation chamber 2 can also be rectangular as can the cross sectional shape of the heating element 3. The heating element 3 is typically positioned and orientated so as to optimise the efficiency with which the stream of carrier gas entering the first inlet 1 is saturated with the working fluid vapour.

Figure 5:
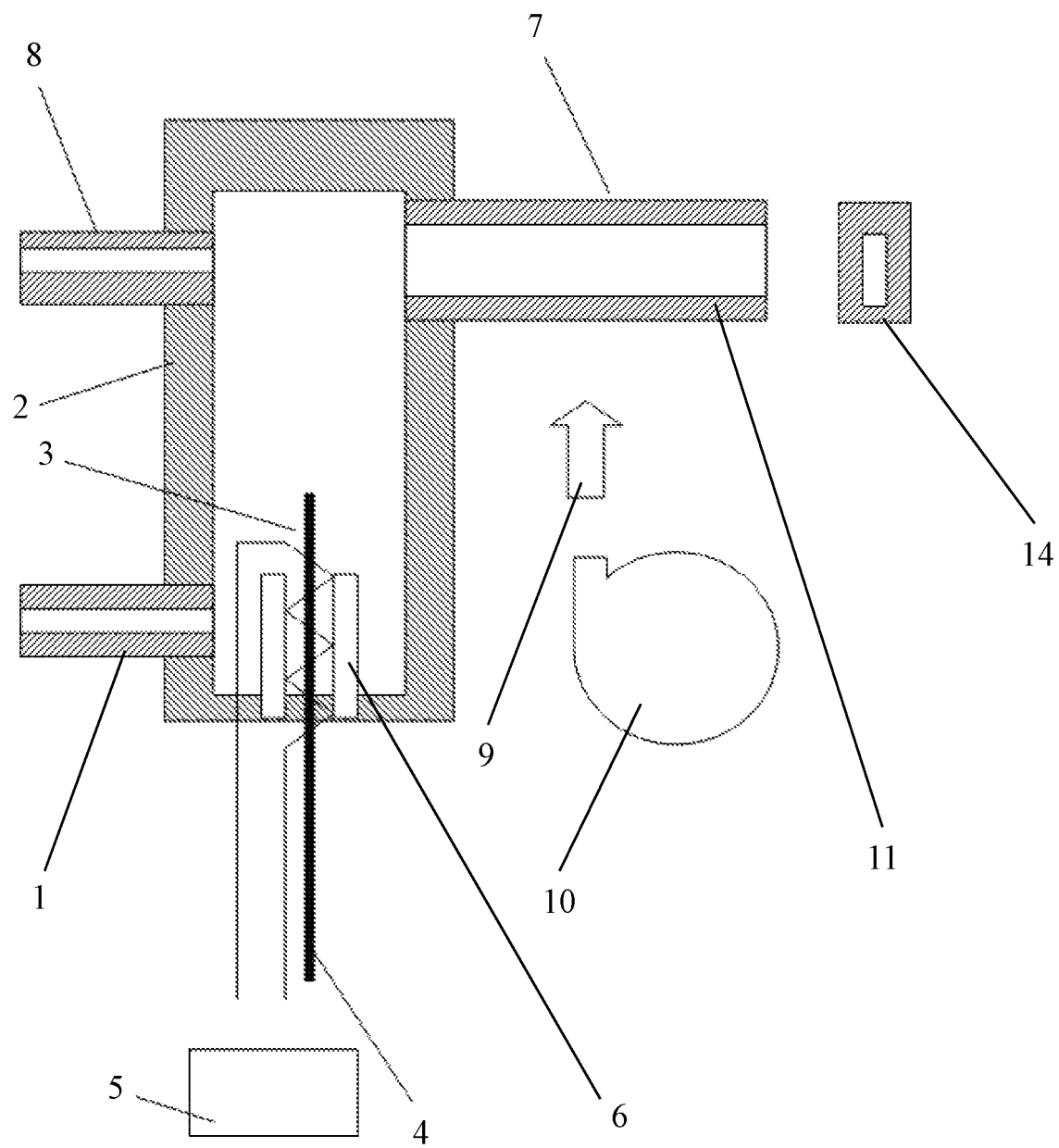
FIG. 5 is a schematic view of a condensation apparatus according to a fourth embodiment of the invention.

If the width of the rectangular cross section condenser shown in FIG. 5 is small (e.g. less than 2 mm), then there is a risk that condensed working fluid will build up on the interior surface of the condenser thereby clogging the condenser. In order to prevent this from happening, means can be provided for removing condensed working fluid form the condenser. One way of doing this is to remove the condensed liquid from the internal surfaces of the condenser by means of a combination of a capillary action and a pressure differential. An arrangement for accomplishing this is shown in FIG. 6.

Figure 6:
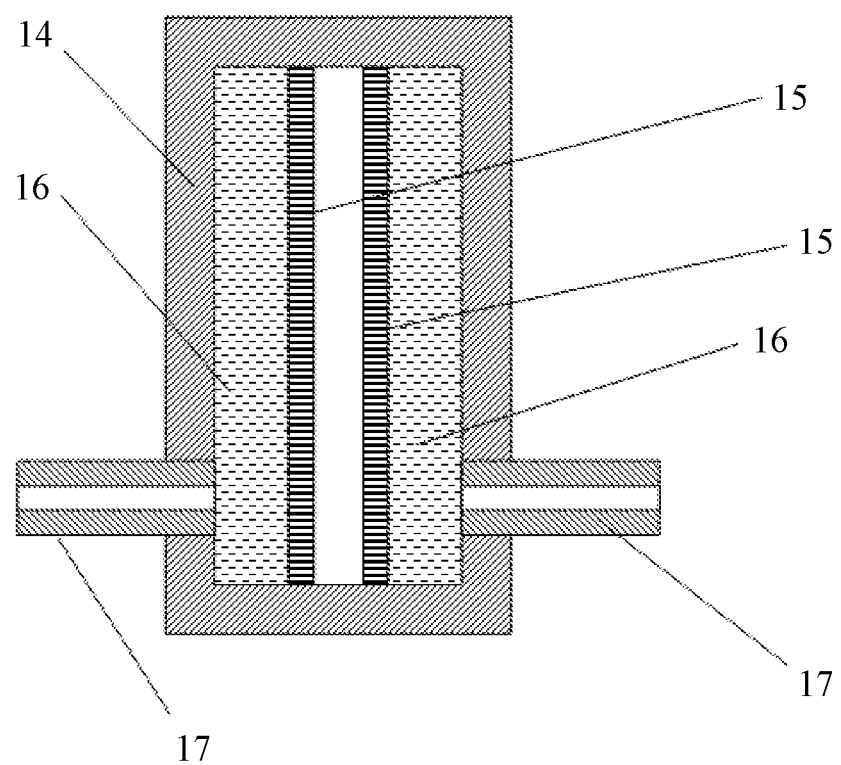
FIG. 6 is a schematic side sectional elevation of a rectangular cross section condenser/outlet provided with working fluid removal means that can be substituted for the condenser/outlets of any one of the embodiments of FIGS. 2 to 5.

FIG. 6 is a cross sectional view of the condenser. The interior of the condenser is provided with two solid porous membranes 15 which are wettable by the working fluid and serve to partition the interior of the condenser into a central passage and a pair of elongate fluid collection chambers 16. In use, as the stream of vapour and gases containing the nano-particles and growing droplets passes along the central passage between the membranes 15, condensation of working fluid vapour onto the surface of the membranes takes place. The excess liquid thus formed is immediately sucked through the membranes 15 and into the collection chambers 16 by the combination of capillary action and a negative pressure maintained by a pump (not shown). From the chambers 16, the liquid is removed through the outlets 17 and can then be directed to a waste collection chamber (not shown) or, in the case of an apparatus having a working fluid reservoir 12 as shown in FIG. 3, recycled to the reservoir.

It is advantageous to control the temperature of the liquid in the working fluid containers 16 to stabilise the temperature of the condenser. This can be done using an external cooling element (e.g. thermoelectric cooling element) as shown in FIG. 4 or can be achieved by circulating the liquid through a heat exchanger as shown in FIG. 7.

Figure 7:
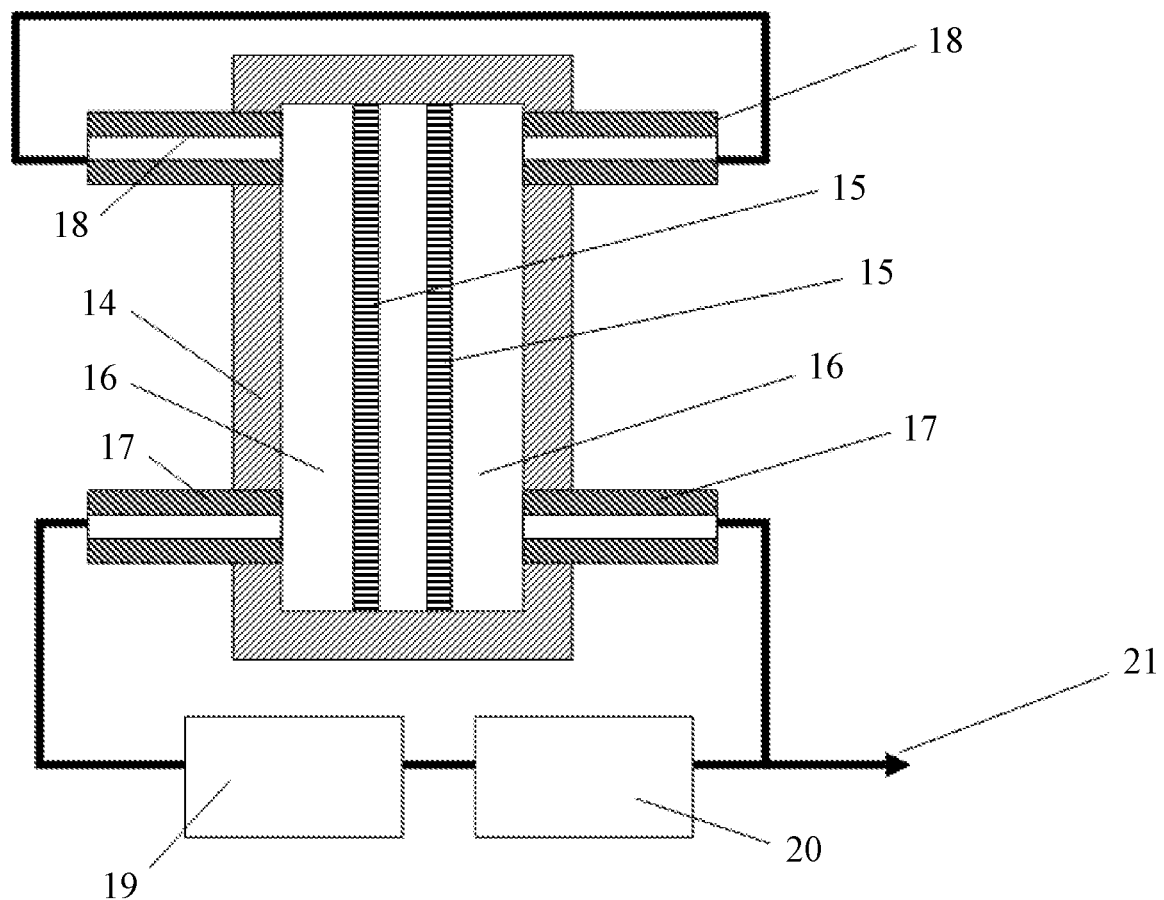
FIG. 7 is a schematic side sectional elevation of an alternative rectangular cross section condenser/outlet provided with working fluid removal means that can be substituted for the condenser/outlets of any one of the embodiments of FIGS. 2 to 5.

FIG. 7 is a schematic illustration of a cross-section of part of a condenser (the rest of the condenser is not shown) provided with fluid collection chambers 16 which are connected to a working fluid recycling and temperature control circuit.

The chambers 16 each have an additional outlet 18 and the two outlets are connected by a length of tubing. The inlets/outlets 17 are connected via lengths of tubing to a pump 19 and a temperature controller 20. Together, the inlets/outlets 17 and 18, the connecting tubing, the pump 19 and the temperature controller 20 form a circuit around which the working fluid can be pumped. The working fluid flowing around the circuit and through the fluid collection chambers 16 can be maintained at a constant pre-determined temperature by the temperature controller 20 and, in this way, the temperature of the internal surface of the condenser can be controlled.

The circuit is provided with a valve (not shown) that enables a portion of the working fluid to be directed along tube 21 to a reservoir 12 of working fluid in the main body of the evaporation chamber 2 by means of an additional pump (not shown) or other liquid transporting means.

The tubing connections shown in FIG. 7 are merely illustrative and it will be appreciated that the connections can be arranged differently to enable the liquid to cool the condenser more uniformly. For example, in an alternative arrangement, the working fluid can be directed from the controller 20 to the inlets 17 and removed from outlets 18 to the pump 19.

In addition, it should be appreciated that the left and the right fluid collection chambers 16 can be maintained at different temperatures. This generates extra supersaturation of the vapours of the working fluid in the condenser and enables the rate of growth of the droplets and the droplet size to be increased or decreased as required. In this case each chamber has its own temperature controlling cycle. The temperatures of liquid in the containers can be found experimentally by means of trial and error or calculated according to nucleation theory.

Keeping two fluid collection chambers 16 at different temperatures has another important advantage. When supersaturation in the condenser is sufficiently high, nano-particles of different sizes can form droplets in different locations along their travel through the condenser and, therefore, droplets formed onto nano-particles of different sizes will grow to various sizes. For instance, 50 nm particles will produce 0.5 µM droplets but 100 nm particles will generate 1 µm droplets. This enables the size of the nano-particles to be obtained from the size of the droplets, a facility which can form the basis for methods of characterising aerosol size distributions.

It should be also appreciated that the temperature of the internal surface of the condenser can be non-uniform, for instance, it can linearly decrease with the length of the condenser. This gradually increases supersaturation of the working fluid vapour along the length of the condenser and, therefore, increases the ability of the apparatus to grow nano-particles of different sizes up to droplets of different sizes. Larger nano-particles tend to form droplets earlier (at the beginning of the condenser) whereas smaller particles that require greater supersaturation tend to form droplets only later at the end of the condenser and consequently the smaller particles have less time to grow and therefore grow to smaller droplet sizes in comparison with larger nano-particles. This makes it possible to establish a one-to-one relationship between the size of droplets formed in the condensation chamber and the size of nano-particles. This relationship can be utilised to evaluate the size of nano-particles by analysing the size of the droplets.

Supersaturation in the apparatus of the invention is controlled by the temperature of the walls, the dimensions of the component parts of the apparatus and the flow rates of the carrier gas and sample gas streams through the apparatus. Variation of these parameters enables a skilled person to select the supersaturation conditions. There is a well-known link between the supersaturation and the minimal size of nano-particles that can form droplets. Therefore, it is possible to change the lower detection limit of a condensation apparatus by changing one or several of these parameters, e.g. the temperature of a heating element 3. This is a powerful tool iii determining size distributions of nano-particles and the proportion of nano-particles in various size ranges. It also enables the development of a condensation apparatus with a predetermined lower detection limit, e.g. 100 nm, 30 nm, 10 nm or 3 nm or with a variable lower detection limit. This provides a platform for an aerosol particle sizing in order to obtain nano-particle size distributions.

It also should be appreciated that a plurality of condensation apparatuses of the invention set up to give different supersaturation conditions can be connected to each other sequentially or in parallel. The sequential arrangement enables nano-particles of different sizes to grow up to different size droplets. If the first condensation chamber is set at lower supersaturation than the second then larger particles form droplets in the first chamber but smaller particles form droplets only in the second chamber whereas previously formed droplets are grown further and become distinctly larger in size. The same is true for the second and the third chambers. Thus, a plurality of chambers enables a plurality of droplet sizes to be formed. This allows the size distribution of nano-particles to be retrieved by analysing the size distribution of droplets, e.g. by using an optical particle counter.

In the case of a parallel arrangement of condensation chambers, the stream of nano-particles of interest is divided into several parallel flows and the said flows are directed to different chambers. The chambers should be set to different values of supersaturation so as to have different lower size detection limits. This makes it possible to retrieve nano-particle number size distributions by analysing the numbers of droplets grown in these chambers.

It will also be appreciated that it is possible to vary temperatures and other parameters of the condensation apparatus and therefore vary the supersaturation as well as the lower detection limit during a given measuring cycle. This enables a cumulative particle size distribution to be obtained.

Figure 8:
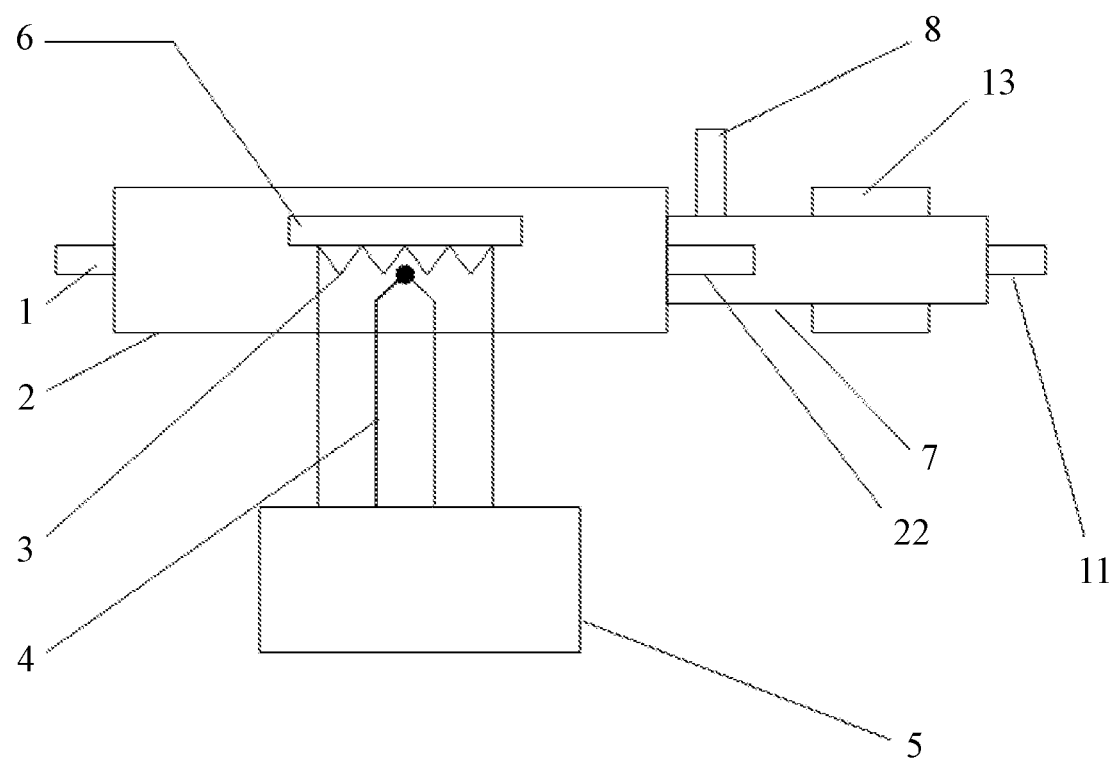
FIG. 8 is a schematic view of a condensation apparatus according to a fifth embodiment of the invention.

An apparatus according to a further embodiment of the invention is illustrated schematically in FIG. 8. In this embodiment, the apparatus comprises an evaporation chamber (saturating chamber) 2 containing a heating element 3 powered by a controlled power supply 5. The heating element 3 is in close contact with a porous material 6 soaked with a working fluid, e.g. semi-volatile compound, attached to a temperature sensor 4 connected to the power supply 5. The evaporation chamber has an inlet 1 and an outlet which extends into a nozzle 22 opening into the condenser 7. The condenser is provided with an inlet 8 through which a gas sample containing nano-particles of interest can be introduced into the condenser. The nozzle 22 extends into the condenser so that it opens out into the condenser downstream of the inlet 8. The condenser 7 is equipped with an outlet 11 and a cooling element 13.

The embodiment of FIG. 8 works as follows. A stream of the clean air (carrier gas) is directed into to the saturating chamber 2 via inlet 1 by means of a flow-generating device, e.g. a pump (not shown). In the chamber, the heating element 3 heats the porous material 6 soaked in the working fluid to produce vapour. The air stream containing the vapour is directed to the condenser through nozzle 22 where the air stream is cooled upon mixing with the unheated stream of sample gas containing nano-particles entering through inlet 8. The nozzle 22 is designed to deliver the hot vapour-saturated air stream into the centre of the sample gas stream containing nano-particles so that the hot vapour saturated stream is surrounded by a sheath of cooler sample gas. The combined gas streams are cooled by the cooling element 13 that controls the temperature of the walls of the condensing chamber 7. In the condenser, supersaturation of the working fluid occurs as a result of the mixing of the hot vapour-saturated air with the cooler sample gas and cooling by the walls of the condenser 7. Thus leads to condensation of the working fluid vapour onto the airborne nano-particles and the formation of droplets of about 1 μm. These droplets are directed to an optical particle counter via outlet 11 and counted individually.

In order to reduce particle losses, both the nozzle 22 and the condenser 7 have cylindrical symmetry and the nozzle 22 is positioned along the axis of the condenser 7 in such a way that the end of the nozzle extends downstream beyond the second inlet 8. This enables the cooler sample gas stream to be formed around the vapour-containing carrier gas stream.

An advantage of the condensation apparatus of the invention is that it provides reliable data and can be miniaturised to dimensions much smaller than those of known condensation counters A preferred working fluid in each of the embodiments of the invention is the semi-volatile dimethyl phthalate. A major advantage of using a semi-volatile compound is that it leads to a much lower consumption of working fluid. An apparatus of the invention has been found to work without requiring refilling for more than 10 months.

The choice of flow rates, the temperature of the saturating chamber and the manner in which airborne particles of interest are introduced into the chamber will usually be made according to the nature of the particles and their concentration. The total flow out of the condenser outlet 11 is often in the range from 0.1 to 4 l/min. The clean carrier gas flow accounts for 10 to 90% of the total flow. For dimethyl phthalate, the temperature of the saturating chamber usually is in the range from 80 to 150° C.

In order to reduce the power consumption of the heating element, a thin film heater can be used which has attached to it a porous medium which is wettable by the working fluid. It is advantageous for a part of the porous medium to be long enough to be in contact with working fluid at the bottom of the chamber 2.

The evaporation chamber 2 and condenser 7 may be manufactured from a variety of materials including any metal, glass or ceramic or (in the case of the evaporation chamber) plastics such as PTFE, but it is preferred to use materials or surface treatments that are inert or resistant to oxidation in air or other carrier gases and which do not react chemically with the working fluid. Pyrex glass, quartz, ceramic and stainless steel were used for various modifications of the chambers and their elements.

It will also be appreciated that the sample gas stream containing particles of interest can be introduced through inlet 1 and the clean air via inlet 8. This is preferable for temperature stable particles such as metal particles. However, aerosol particles formed from organic compounds can be affected the high temperatures generated by the heating element and should therefore be introduced via inlet 8.

Figure 10:
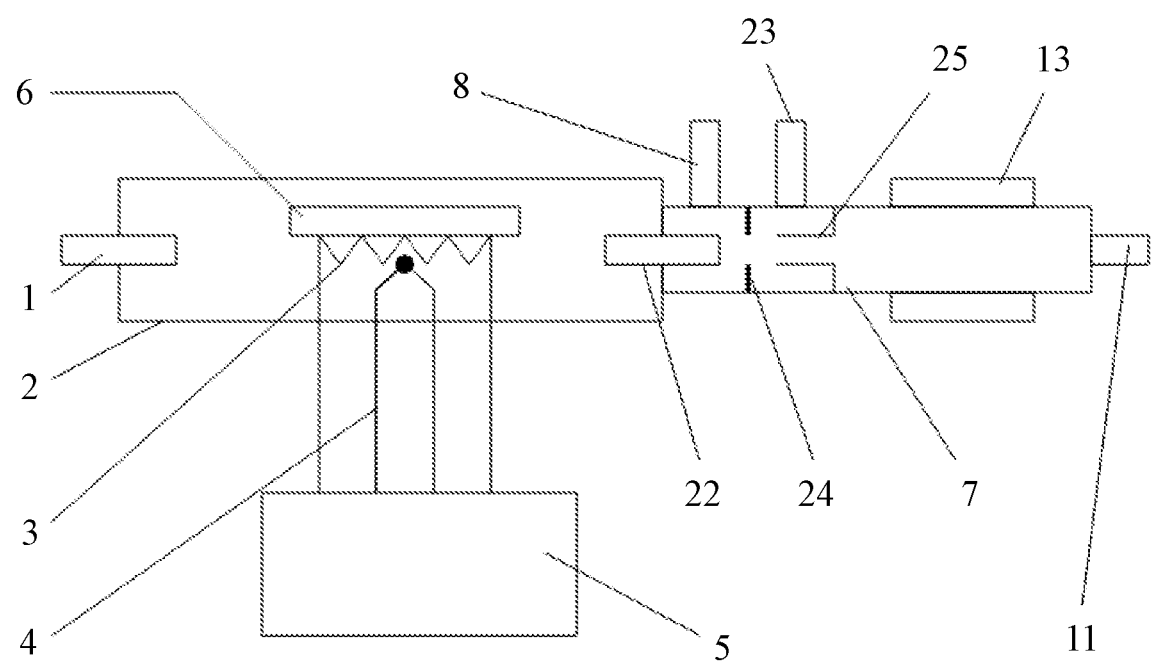
FIG. 10 is a schematic view of a condensation apparatus according to a sixth embodiment of the invention.

An apparatus according to another embodiment of the invention is illustrated in FIG. 10. In this embodiment, in which the evaporation chamber has a similar layout as the embodiment of FIG. 8, a mixing chamber (intermediate chamber) 25 is positioned between the saturating chamber 2 and the condenser 7. The mixing chamber is divided by a partition 24 having a central orifice into a downstream sub-chamber and an upstream sub-chamber. The nozzle 22 extends into the upstream sub-chamber and a cylindrical baffle, which is aligned with the nozzle 22 extends in an upstream direction from the end of the downstream sub-chamber. These elements can be made from the same materials as the rest of the apparatus. The mixing chamber 25 and partition 24 can have cylindrical symmetry or they can be rectangular in cross section. This embodiment enables to achieve the lowest low detection size of nano-particles of 1 nm. A third inlet 23 is provided and this opens out into the annular space surrounding the cylindrical baffle.

In this embodiment, a sample of aerosol of interest is directed into inlet 8 and a stream of clean air is introduced through inlet 23. The mixing chamber enables the stream of the aerosol sample of interest to be sandwiched between a central core stream of carrier gas containing working fluid vapour and a outer layer formed by the clean air from inlet 23. Using an apparatus of this type, it is found that the best results are obtained when the gas layers in the sandwich are cylindrically symmetrical.

Figure 11:
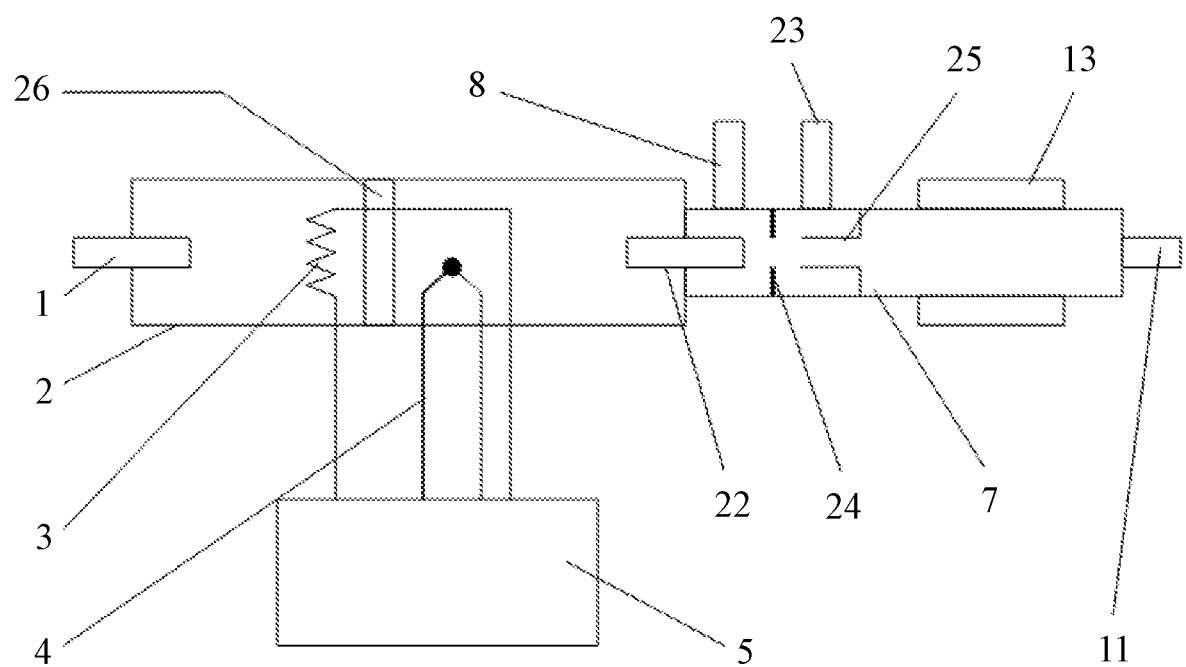
FIG. 11 is a schematic view of a condensation apparatus according to a seventh embodiment of the invention.

It is advantageous to prolong the working life of the apparatus without the need for frequent refilling with working fluid. A significantly longer operating life between refills can be achieved by means of a combination of two condensation units with means for collecting and recycling working fluid from droplets that have passed though the particle detector and which contain airborne particles. Such an assembly can comprise two condensing units and a system of aerosol flow manipulation with three way valves to redirect the flows. The condensation apparatus used with such an assembly is slightly different from the other specific embodiments described above and an example of a suitable condensation apparatus is shown in FIG. 11. In the embodiment of FIG. 11, the inlet 1 receives gas (e.g. air) in which is suspended micro-droplets containing airborne particles recycled from the particle counter. In order prevent the recycled airborne particles from continuing through to the condenser and hence contaminating the sample gas containing the particles of interest, the porous medium 26 is positioned across the evaporation chamber airflow in the evaporation chamber. The porous medium is selected so as to be capable of performing two functions. Firstly, it must be wettable by the working fluid so that, when heated, it can serve as source of vapour and, secondly, it must be capable of functioning as a filter to collect micro-droplets containing microparticles thereby avoiding contamination of the vapour in the region downstream of the porous medium. As in the other embodiments described above, a heating element 3 is positioned near the surface of the porous medium to evaporate deposited working fluid. However, thermal contact between the heating element 3 and the porous medium 26 is not important in this embodiment because of the heating effect provided by the gas entering the chamber through inlet 1.

It should be understood from the above that the porous medium 26 should be positioned in such a way to form an airtight seal with the walls of the evaporation chamber so that all of the gas received through inlet 1 is filtered and all of the airborne particles are trapped. Droplets of working fluid collected on the porous support can be re-evaporated and released as vapour into the evaporation chamber on the downstream side of the porous support An assembly comprising two condensation apparatuses of the aforementioned type consumes negligible or no working fluid and therefore does not need to be refilled. Such an assembly is illustrated in FIG. 12.

Figure 12:
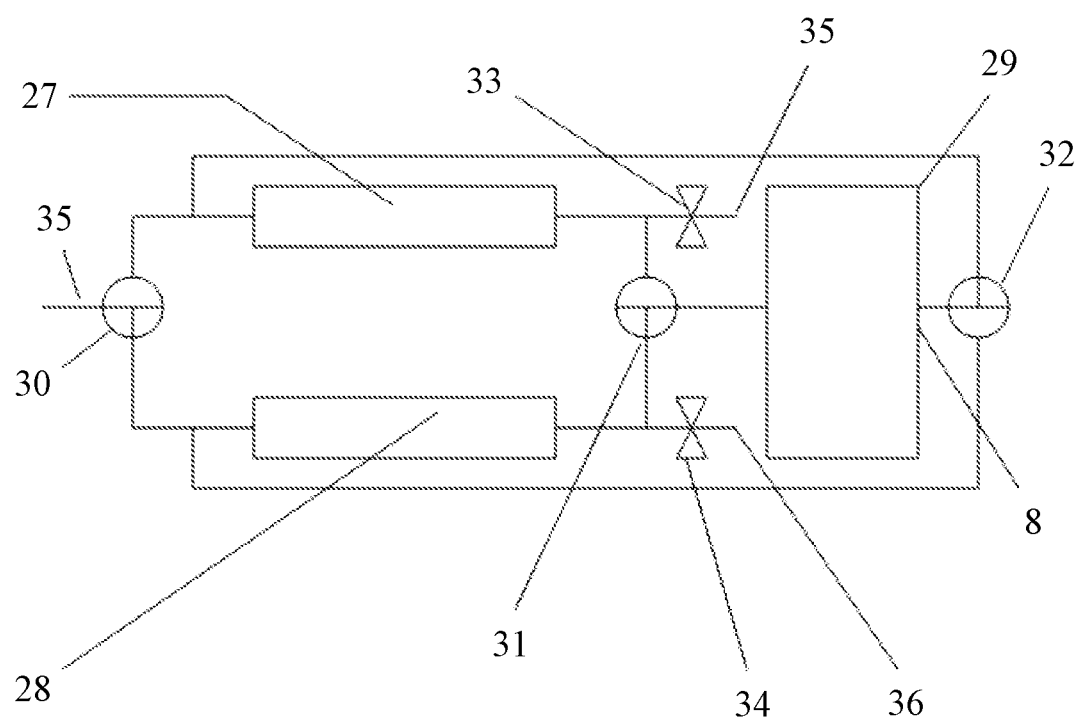
FIG. 12 is a schematic representation of a condensation apparatus and particle counter assembly according to an eighth embodiment of the invention, wherein the assembly has the ability to recycle working fluids.
Figure 13:
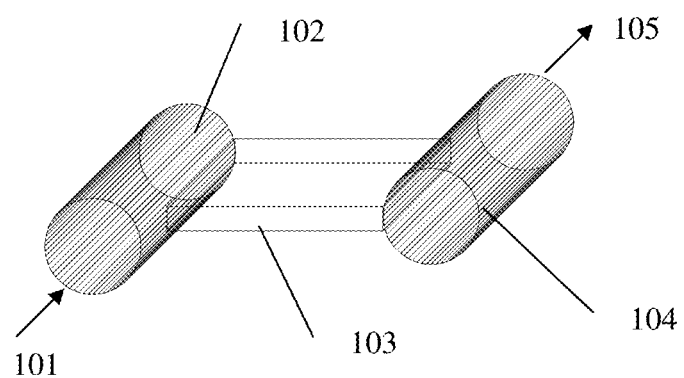
FIG. 13 is a schematic view of the rectangular condenser with a flow distributor in the entrance to the condenser and in the outlet of the condenser.
Figure 14:
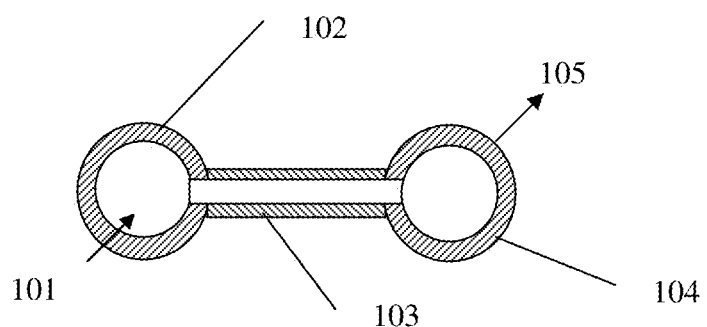
FIG. 14 is a cross-sectional view (vertical plane) of the rectangular condenser with a flow distributor in the entrance to the condenser and in the outlet of the condenser.
Figure 15:
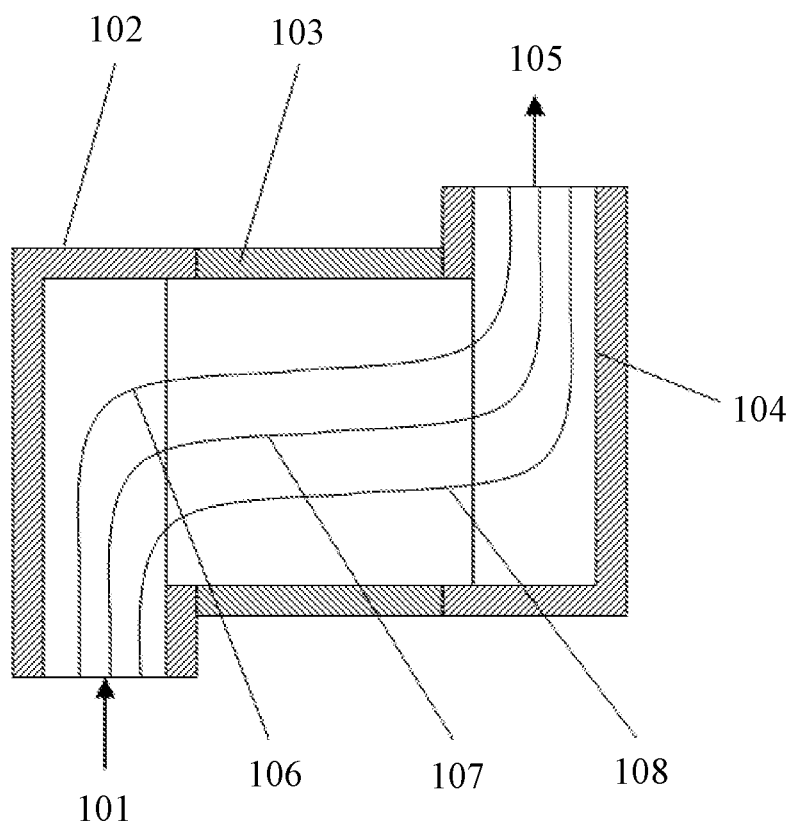
FIG. 15 is a cross-sectional view (horizontal plane) of the rectangular condenser with a flow distributor in the entrance to the condenser and in the outlet of the condenser.
Figure 16:
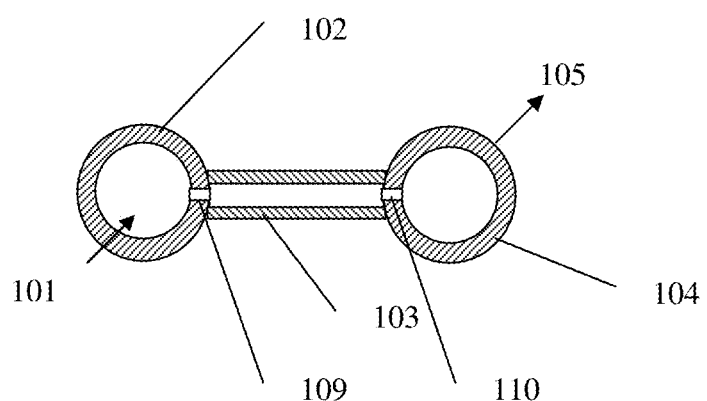
FIG. 16 is a cross-sectional view (vertical plane) of the rectangular condenser with a flow distributor containing a slot in the entrance to the condenser and another flow distributor with a slot in the outlet of the condenser.

The assembly shown in FIG. 12 comprises two apparatus 27 and 28 each corresponding to the apparatus illustrated in FIG. 11 and an optical particle counter 29. Three three-way valves 30, 31 and 32 and two on/off valves 33 and 34 direct the flows of fluid to permit recycling of the working fluid.

The assembly shown in FIG. 12 functions as follows:

Airflow containing nano-particles of interest is drawn via common inlet 35 into one condensation apparatus (e.g. apparatus 28) by appropriate adjustment of the three-way valve 30. Micro-droplets formed on the nano-particles in the apparatus are directed towards optical particle counter 29 by means of three-way valve 31 while valve 34 is closed. After being counted, micro-droplets are directed to the other apparatus 27 by three-way valve 32. In apparatus 27, micro-droplets are collected onto the porous medium and filtered clean air is released into the atmosphere through outlet 35 by opening valve 33. The evaporation chamber in apparatus 27 remains cold because there no voltage is applied to the heating element, and therefore the working fluid collected on the porous medium is stored.

After an appropriate period of time, the apparatus 27 is heated, the valve positions are adjusted and apparatus 28 is allowed to cool so that it is able to collect droplets of working fluid. The previously idle apparatus 27 is then in working mode and the working fluid previously captured by the porous medium is heated and evaporated to form a vapour which is then mixed with a gas sample stream as described above.

After passing through the condenser and particle counter, the stream of particle- and vapour-laden air is directed to apparatus 28 where the air is filtered and the working fluid collected as described above for apparatus 27. The cycle is then repeated.

The time necessary to switch between the chambers can be determined empirically through trial and error. Normally it is only necessary to switch the valves after hundreds of hours of operations. Therefore, the system requires relatively little energy to operate and energy and can be easily implemented.

If necessary, additional specialised gas filters can be attached to outlets 35 and 36 to trap working fluid vapour remaining in the gas stream after filtration by the porous support. However, by using a semi-volatile working fluid such as dimethyl phthalate, for the majority of applications there is no need to use additional filters because the vapour pressure of the semi-volatile compound is very low.

In each of the foregoing embodiments, the condensation chamber can be equipped with a working fluid sensor, e.g. filled glass capillary or dew point type sensors (not shown in the Figures). A sensor placed e.g. inside the chamber enables the depletion of the working fluid to be monitored.

FIGS. 13 to 16 illustrate a further type of condenser for use in the apparatus of the invention. In this embodiment, the condenser is of rectangular cross section.

By using a condenser of rectangular cross-section, the size of the condensation chamber can be reduced considerably. However, a potential problem with some rectangular condenser layouts, particularly where the inlet and outlet of the condenser are tubes of circular cross section, is that there may be non-uniformity of the flow velocity in the condenser. This can lead to some particles spending more time in the condenser than others meaning that there is non-uniform growth of the particles in the condenser. This in turn can give rise to inaccuracies in measurement of the numbers and sizes of the particles. FIGS. 13 to 16 illustrate a rectangular condenser which provides a substantially uniform flow velocity of the vapour laden gases through the condenser. In this embodiment, a pair of flow distributors is provided, one attached either side of the rectangular condenser. One of the flow distributors is in fluid communication with (e.g. connected to) the evaporation chamber, and the other flow distributor is in fluid communication with (e.g. is connected to) a particle detector.

Thus, as shown in FIG. 13, a rectangular condenser 103 is equipped with the first flow distributor 102 and a second flow distributor 104, both of which are in fluid communication with the condenser. The hot gas (e.g. air) saturated with working fluid enters the first flow distributor 102 via an inlet 101. The flow distributor 101 is designed to supply a uniform flow to the condenser 102. Therefore, the opposite to the inlet 101 end of the flow distributor 102 is blocked, see FIG. 15. At the outlet of the condenser 103, the second flow distributor is attached to reduce non-uniformity of the flow at the outlet of the condenser 103. The gas flow leaves the second flow distributor through an outlet 105.

FIG. 14 shows the relative positions of the first flow distributor 101, the rectangular condenser 103 and the second flow distributor 104.

FIG. 15 shows schematically the flow stream lines inside the condenser 103, the flow distributor 102 and the flow distributor 104. In this embodiment, the air parcels moving along trajectories 106, 107 and 108 have substantially the same velocity and therefore substantially the same residence time in the rectangular condenser 103 and as a result substantially the same sizes of droplets formed.

The uniformity of the residence time is achieved by designing the flow distributors such that the internal area of the cross-sections of the flow distributors are sufficiently greater than the internal area of the cross-section of the condenser. As an example, if the cross-section of the flow distributors is a circle of the internal diameter Dt and the condenser internal height is Hc and the internal width Wc then $\pi Dt^2 > Hc*Wc$. The ratio of $\pi Dt^2/(Hc*Wc)$ should be more than 1.1 or preferably more than 2 or even more preferably the ratio should be more than 3.

Fluid communication between the interiors of the flow distributors 102 and 104 and the interior of the rectangular condenser can be achieved by providing the walls of the flow distributors with elongate narrow slots or a linear array of holes that open into the condenser. It is advantageous to provide a narrow slot between the flow distributors 102 and 104 and the condenser 103. In FIG. 16, the vertical cross-sectional view shows schematically the slots 109 and 110. In this case the internal diameter of flow distributors can be reduced because of the uniformity of the flow in the condenser is governed by the expression containing the width of the slot Ws but not the height of the condenser Hc: $Hc > Ws$. The ratio of $Hc/Wc$ should be more than 1.1 or preferably more than 2 or even more preferably the ratio should be more than 3.

In another embodiment, the flow distributor contains holes evenly distributed along the inlet and outlet of the rectangular condenser 103 instead of two slots. The number of holes Nh should be more than 1 or preferably more than 4 or even more preferably more than 10. The diameter of the holes Dh should be sufficiently small and can be evaluated from the expression: $\pi Dt^2 > Nh*\pi Dh^2$. The ratio of $\pi Dt^2/(Nh*\pi Dh^2)$ should be more than 1.1 or preferably more than 2 or even more preferably the ratio should be more than 3.

In one embodiment of the condenser arrangement shown in FIGS. 13 to 16, the flow distributors 102 and 104 were manufactured from a stainless steel tube of 7 mm ID and the length of 40 mm. The condenser 103 was manufactured from stainless steel sheet with dimensions: Wc=20 mm, Hc=1.4 mm and Lc=30 mm. However, it should be appreciated that other materials can be used to manufacture the flow distributors, e.g. PTFE, aluminium, or any suitable metal, glass, ceramic or plastics material.

It will also be appreciated that the shape of the cross-section of the distributor may be rectangular, triangular, ellipsoidal, polygonal or any combination of simple geometric shapes.

Figure 17:
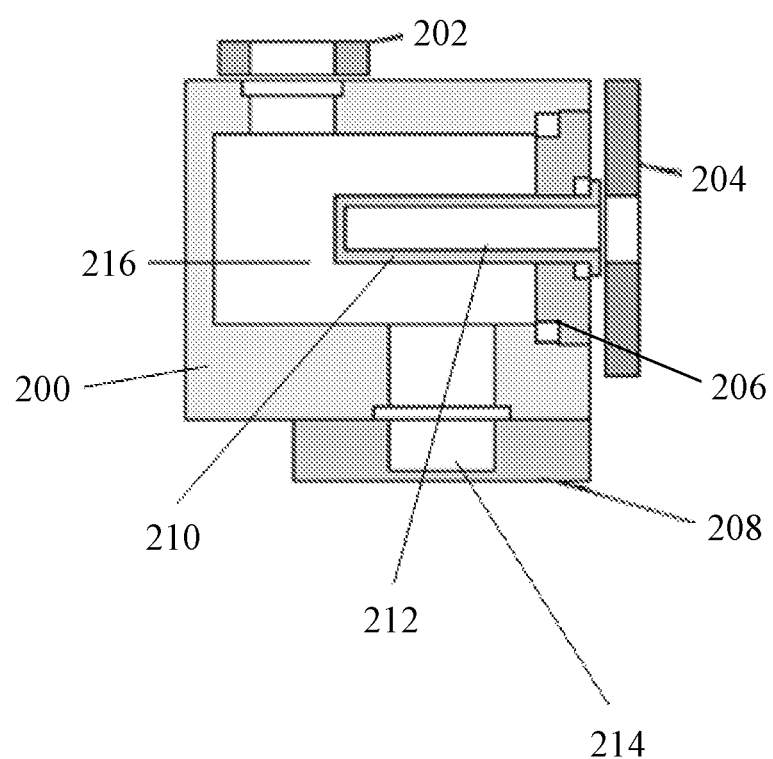
FIG. 17 is a sectional view through an evaporation chamber according to another embodiment of the invention.
Figure 18:
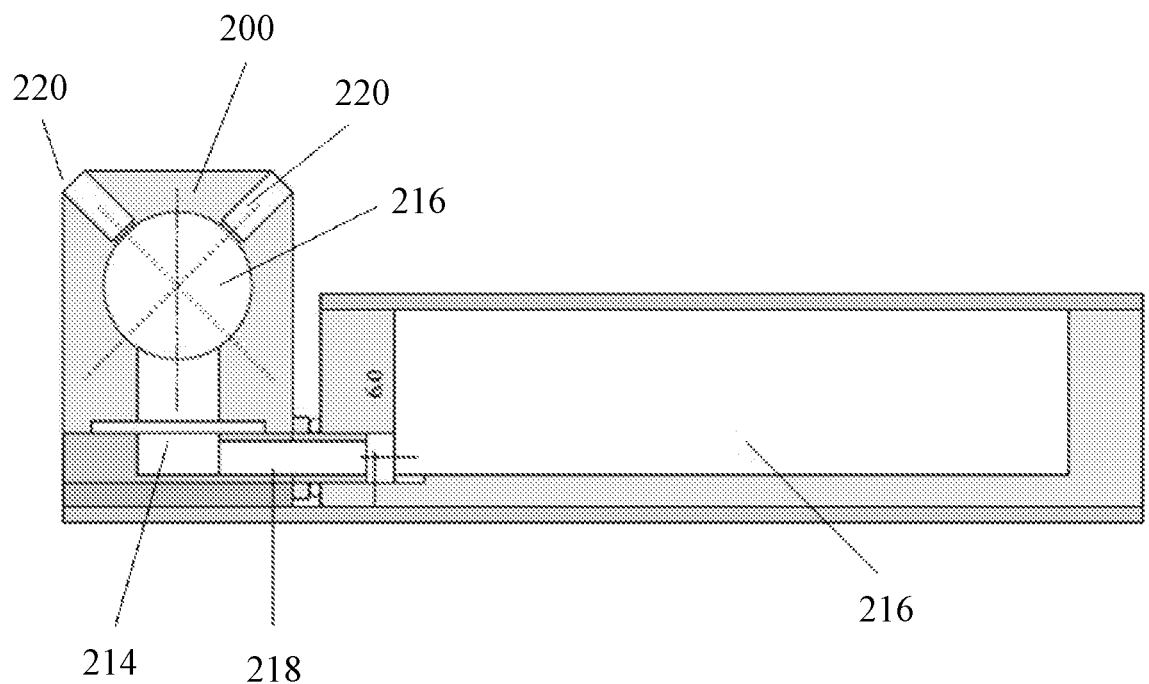
FIG. 18 is a schematic sectional elevation showing the evaporation chamber of FIG. 17 from another angle but with the heating element omitted and a working fluid reservoir in place.
Figure 19:
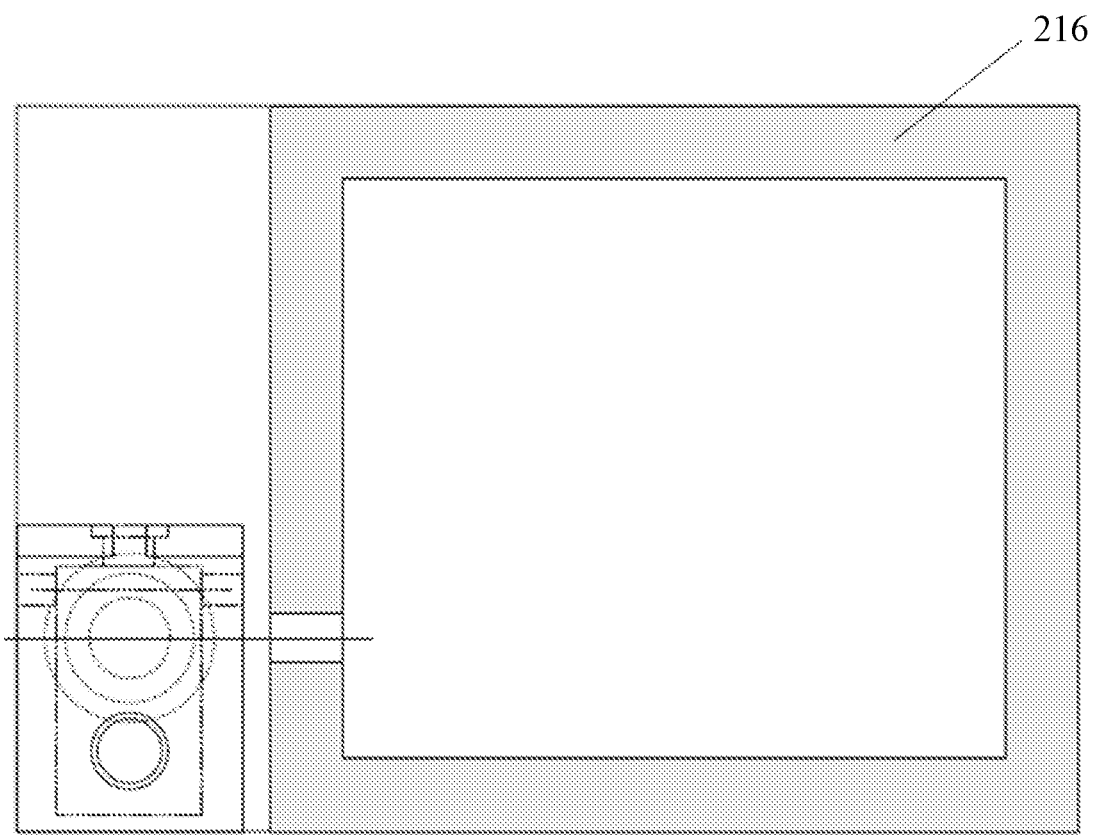
FIG. 19 is a schematic sectional elevation showing a plan view of the apparatus depicted in FIG. 18.

FIGS. 17 to 19 illustrate an evaporation chamber and associated working fluid reservoir.

The evaporation chamber shown in FIG. 17 comprises a body 200 formed from PTFE enclosing a chamber interior 216. The chamber has a pair of inlets 220 (not shown in FIG. 17 but see FIG. 18) and has means 202 for connection to a condenser (not shown).

A heating element is mounted in one side of the PTFE body 200. The heating element has a mounting portion 206 removably secured in the wall of the PTFE body, and a rod portion 210 which extends into the chamber interior 216. A holder 204 holds the mounting portion 206 in place and an O-ring provides a seal between the mounting portion 206 and the wall of the chamber body. Another O-ring provides a seal between the mounting portion 206 and the rod 210.

Figure 20:
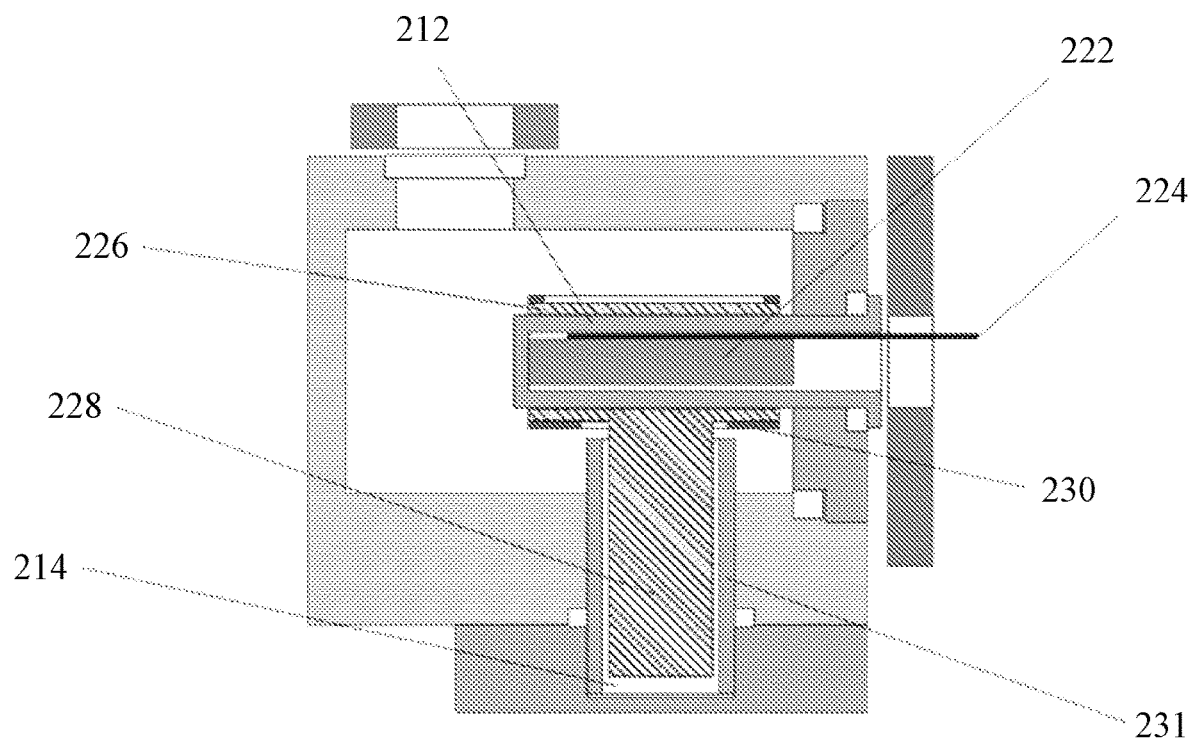
FIG. 20 is a more detailed sectional elevation of the heating element and porous support used in the embodiment of FIGS. 17 to 19.

The rod portion 212 has a hollow interior within which are disposed a metal heating wire 222 and a thermocouple 224 (see FIG. 20). The heating wire 222 and thermocouple 224 are secured in place by means of a thermal filler (222) which can be, for example, a solder or a metal filled epoxy resin.

The heating wire and thermocouple are connected to a controller (not shown).

Beneath the heating element, the body of the evaporation chamber has a well 214/218 for holding a working liquid such as dimethyl lphthalate. The well 214/218 is connected via tube 218 (see FIG. 18) to a reservoir 217 of the working fluid.

As shown in FIG. 20, the rod portion is surrounded by a sleeve 226 of a porous material which, in this embodiment, is a porous fabric such as quartz fibre filter or glass fibre filter or a polymer or metal filter. The sleeve of porous fabric has a tail portion 228 which extends into the well and acts as a wick to draw working fluid up from the well. The sleeve is held in place on the rod portion by means of a clip 230 which is provided with holes through which the working liquid can evaporate and an an opening on its underside to accommodate the tail portion of the sleeve. The wick is surrounded by a wick holder 231 made from an inert material e.g. stainless steel.

In this embodiment, the heating element is in direct contact with the porous support thereby reducing the heat input required and time taken to evaporate the working fluid to form a saturated vapour within the chamber.

EXAMPLES

Several examples of apparatus according to this invention have been built and tested and these are described below.

Example 1

In one example constructed as shown in FIG. 8, the evaporation chamber (saturating chamber) 2 was made of stainless steel tube (12 mm ID) and 30 mm length. Stainless steel tube of 3 mm ID was used for the inlets, nozzle and the outlet. The cooling element was constructed from a 5V DC micro fan positioned at 15 mm from the surface of the condensing chamber. The condenser chamber was made of stainless steel tube 6 mm ID length 60 mm and the heating element was made a NiCr heating element covered with a quartz fibre material that was sufficiently long to be positioned near to the bottom of the stainless steel cylinder of the saturating chamber. About 0.5 ml of dimethyl phthalate was poured into the chamber 2 as the working fluid. Micro droplets formed onto nano-particles were counted with a MetOne laser optical particle counter. The apparatus was tested against SMPS (TSI), portable SAC size spectrometer (Naneum) and a handheld instrument 3007 CPC (TSI, model 3007). Nanoparticles of chromium oxides and atmospheric aerosols were used for the tests. In the tests, it was found that the apparatus of the invention enabled nano-particles to be enlarged up to 1.2 μm in diameter and the lower limit of the detection range was estimated to be 4 nm.

Example 2

A comparison was made between aerosol particle number concentrations (N) measured using an apparatus as illustrated in FIG. 2 coupled to a MetOne laser optical particle counter and aerosol particle number concentrations (N) measured using a handheld 3007 CPC from TSI. The clean air flow through inlet 1 into the saturating chamber was set at 0.3 l/min and the sample gas flow through inlet 8 was set at 0.5 l/min. Nano-particles of chromium oxide and atmospheric aerosols were used for the comparative tests.

Figure 9:
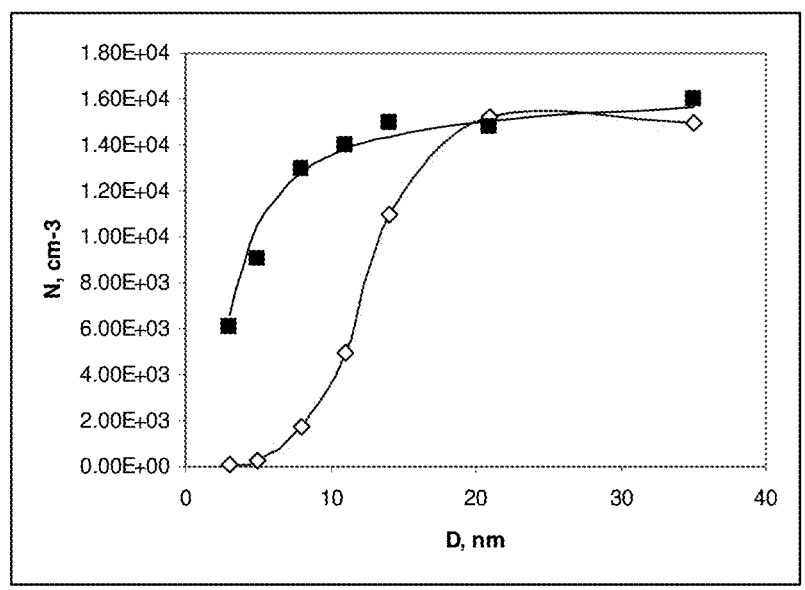
FIG. 9 shows a graph comparing of aerosol particle number concentrations (N) measured with the condensation chamber of FIG. 2 coupled with a MetOne™ laser optical particle counter (black squares) and handheld 3007 CPC from TSI (white diamonds).

The results are shown in FIG. 9 where the data points for the apparatus of the invention are shown as black squares and the data points for the TSI 3007 CPC instrument are shown as white diamonds. In FIG. 9, D is the mean diameter (nm) which was obtained by calibration using a reference method.

It was found that the apparatus of the invention enables nano-particles to be enlarged up to 1.2 μm in diameter. The lower detection limit for the apparatus of the invention was estimated to be 3 nm. It is clear from FIG. 9 that the lower detection limit of the apparatus of the invention is lower than the low detection limit of CPC 3007 (TSI).

EQUIVALENTS

It will readily be apparent that numerous modifications and alterations may be made to the specific embodiments of the invention described above without departing from the principles underlying the invention. All such modifications and alterations are intended to be embraced by this application.

The invention claimed is:

1. An apparatus for increasing the effective size of gas-entrained particles in a particle detector, the apparatus comprising:
   an evaporation chamber;
   a heating element and a porous support each of which is disposed within the evaporation chamber, the porous support carrying thereon a working fluid and the heating element configured to vaporize the working fluid to form vapor within the evaporation chamber;
   wherein the porous support surrounds the heating element; a working fluid reservoir disposed in the evaporation chamber, the working fluid reservoir being configured to hold a working fluid, wherein the porous support includes a portion which extends into the working fluid reservoir;
   a condenser in fluid communication with the evaporation chamber for receiving said vapor; the condenser having an outlet for connection to a panicle detector; and an inlet in fluid communication with the condenser for receiving a stream of sample gas containing gas-entrained particles; the apparatus being configured so that condensation of the vapor onto the gas-entrained particles in the sample gas takes place in the condenser to increase the size of the particles for detection by a particle detector.

2. The apparatus of claim 1, wherein the inlet is provided in fluid communication with evaporation chamber, wherein the inlet is configured such that the stream of sample gas is mixed with the vapor in the evaporation chamber and is transported through the condenser.

3. The apparatus of claim 1, comprising a temperature sensor disposed within the evaporation chamber.

4. The apparatus of claim 1, comprising a cooling means operationally connected to the condenser to provide cooling of a mixture of gases, vapor and particles in the condenser.

5. The apparatus of claim 1, wherein the condenser has a surface area to volume ratio greater than the surface area to volume ratio of a cylinder.

6. The apparatus of claim 1, comprising means for removing condensed substance from the interior walls of the condenser.

7. The apparatus of claim 1, comprising means for varying a temperature of the porous support and/or a temperature of the condenser or its parts.

8. The apparatus of claim 1, wherein the condenser comprises:
a condenser body having a condenser inlet, the outlet, and a hollow interior which has an internal length, an internal width and an internal height; the condenser inlet providing fluid communication with the evaporation chamber;
an inlet flow distributor tube connected to the condenser inlet and extending across the internal width of the condenser body; and
an outlet flow distributor tube connected to the outlet and extending across the internal width of the condenser body;
wherein the internal height of the condenser body is less than a corresponding internal height of each of the inlet and outlet flow distributor tube;
inlet and outlet flow distributor tubes each being provided in the walls of the condenser with one or more slots or holes communicating with the hollow interior of the condenser body so as to provide a flow path from the inlet flow distributor tube through the hollow interior of the condenser and into the outlet flow distributor tube.

9. The apparatus of claim 8, wherein an internal cross sectional area of each flow distributor tube is greater than an internal cross sectional area of the condenser body, wherein the internal cross sectional area of the condenser body is defined as internal width×internal height.

10. A condensation particle counter comprising the apparatus of claim 1.

11. An assembly comprising the apparatus of claim 1 connected to a particle detector.

12. An assembly comprising a plurality of apparatuses of claim 1 connected sequentially or in parallel.

13. The apparatus of claim 1, wherein the heating element comprises a rod portion and the porous support surrounds the rod portion.

14. The apparatus of claim 13, wherein the porous support is formed from a porous fabric and comprises a sleeve that fits over the rod portion of the heating element.

15. The apparatus of claim 13, wherein the rod portion of the heating element has a hollow interior within which is disposed a heater wire or heater probe and a thermocouple.

16. The apparatus of claim 15, wherein a thermally conductive filler is used to hold the heater wire or heater probe and the thermocouple in place.

17. The apparatus of claim 1, comprising a working fluid selected from dimethyl phthalate, dioctyl phthalate and dimethylsulphoxide.

18. The apparatus of claim 1, wherein the evaporation chamber is configured for receiving a stream of carrier gas for carrying vapor through to the condenser.

19. The apparatus of claim 18, wherein the carrier gas is provided by an additional inlet in fluid communication with the evaporation chamber.

20. The apparatus of claim 18, wherein the carrier gas and sample gas are provided by the inlet.

21. The apparatus of claim 1, wherein the heating element is in direct contact with the porous support.

* * * * *